US012673120B2

(12) United States Patent
Wang et al.

(10) Patent No.: US 12,673,120 B2
(45) Date of Patent: Jul. 7, 2026

(54) FLUORESCENTLY-TRACEABLE AMINO ACID DERIVATIVE AND PREPARATION METHODS AND USE THEREOF

(71) Applicant: Capital Medical University, Beijing (CN)

(72) Inventors: Yuji Wang, Beijing (CN); Yanming Wang, Beijing (CN); Di Zhu, Beijing (CN); Yu Lu, Beijing (CN); Botao Liu, Beijing (CN); Aijuan Qu, Beijing (CN); Hao Wu, Beijing (CN)

(73) Assignee: Capital Medical University, Beijing (CN)

( * ) Notice: Subject to any disclaimer, the term of this patent is extended or adjusted under 35 U.S.C. 154(b) by 790 days.

(21) Appl. No.: 18/019,564

(22) PCT Filed: Aug. 3, 2021

(86) PCT No.: PCT/CN2021/110331
§ 371 (c)(1),
(2) Date: Feb. 3, 2023

(87) PCT Pub. No.: WO2022/028421
PCT Pub. Date: Feb. 10, 2022

(65) Prior Publication Data

US 2023/0270889 A1 Aug. 31, 2023

(30) Foreign Application Priority Data

Aug. 3, 2020 (CN) ........................ 202010766644.7

(51) Int. Cl.
*A61K 49/00* (2006.01)
*A61P 35/00* (2006.01)
*C07D 271/12* (2006.01)

(52) U.S. Cl.
CPC ...... *A61K 49/0021* (2013.01); *A61K 49/0052* (2013.01); *A61P 35/00* (2018.01); *C07D 271/12* (2013.01)

(58) Field of Classification Search
CPC . A61K 49/0021; A61K 49/0052; A61P 35/00; C07D 271/12; C07D 413/12; C09B 57/00; C09K 11/06; C09K 2211/1007; C09K 2211/1029; C09K 2211/1048; G01N 21/6428; C07B 2200/07
See application file for complete search history.

(56) References Cited

U.S. PATENT DOCUMENTS

2020/0002322 A1 1/2020 Hamase et al.

FOREIGN PATENT DOCUMENTS

| | | | |
|---|---|---|---|
| CN | 104478823 | A | 4/2015 |
| CN | 110366552 | A | 10/2019 |
| CN | 111848544 | A | 10/2020 |
| JP | S61129175 | A | 6/1986 |

OTHER PUBLICATIONS

International Search Report for Application No. PCT/CN2021/110331 mailed Nov. 3, 2021, 4 pages.
Ruan M. et al., "Preparation and evaluation of tert-leucine derivative functionalized polymeric monoliths for micro-liquid chromatography", Electrophoresis, Jul. 19, 2017 (Jul. 19, 2017), pp. 3020-3028, vol. 38, No. 22, ISSN: 0173-0835.
Sato E. et al., "A Potentially Useful Fluorogenic Amine, 4-Amino-7-nitrobenz-2-oxa-1,3-diazole. An Application as a Substrate for a Microdetermination of Chymotrypsin", Chem. Pharm. Bull, Jan. 25, 1984 (Jan. 25, 1984), pp. 336-339, vol. 32. No. 1, ISSN: 0009-2363.
Zhao, H. "Determination of the Four Threonine Isomers and Isoleucine in Mammals", Wanfang Theses and Dissertations, Jul. 25, 2007 (Jul. 25, 2007), pp. 1-93. [Providing English Translation of Abstract only pp. 6-7].

*Primary Examiner* — Robert S Cabral
(74) *Attorney, Agent, or Firm* — Lerner David LLP

(57) ABSTRACT

The present disclosure provides a fluorescently-traceable amino acid derivative and a preparation method and use thereof, and belongs to the technical field of biomedicine. In the present disclosure, an amino acid skeleton of the amino acid derivative is modified mainly by a fluorescently-traceable functional group. 4-chloro-7-nitro-2,1,3-benzoxadiazole (NBD-Cl) has low polarity and strong fluorescence, and can be used to modify an N-terminal of the amino acid skeleton to conduct subcellular imaging. Moreover, the NBD-Cl has a relatively small volume, lacks reaction orthogonality, and causes little interference with biochemical reactions of the organism itself. The results of examples show that the fluorescently-traceable amino acid derivative has a desirable biological activity and can be fluorescently traced in vivo and in vitro.

20 Claims, 10 Drawing Sheets

A

B

C

D

E

F

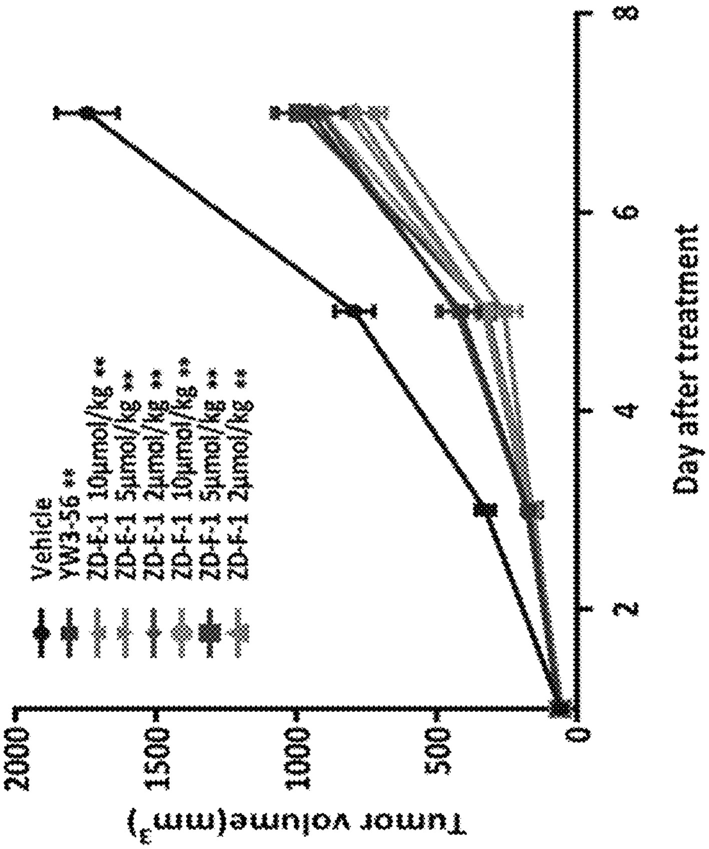
FIG.4
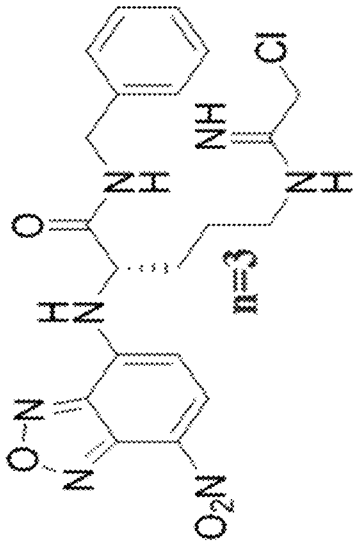
n=3
ZD-E-1
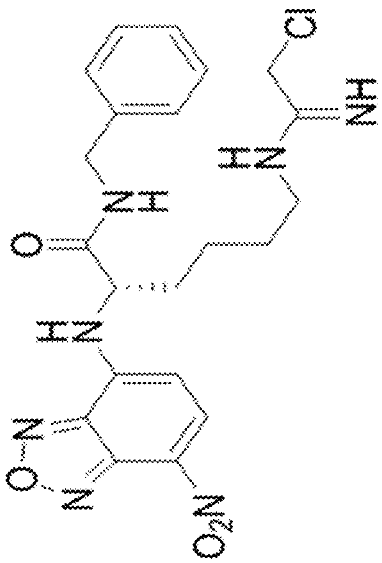
ZD-F-1

FLUORESCENTLY-TRACEABLE AMINO ACID DERIVATIVE AND PREPARATION METHODS AND USE THEREOF

CROSS REFERENCE TO RELATED APPLICATION

The present disclosure is a U.S. National Phase application that claims priority to PCT/CN2021/110331 filed Aug. 3, 2021, which claims priority to Chinese Patent Application No. 202010766644.7 filed to the China National Intellectual Property Administration (CNIPA) on Aug. 3, 2020 and entitled "FLUORESCENTLY-TRACEABLE AMINO ACID DERIVATIVE AND PREPARATION METHODS AND USE THEREOF", which is incorporated herein by reference in its entirety.

TECHNICAL FIELD

The present disclosure relates to the technical field of biomedicine, and in particular to a fluorescently-traceable amino acid derivative and a preparation method and use thereof.

BACKGROUND

In recent years, remarkable progress has been made in the fight against cancer. However, cancer is still an extremely serious public health challenge to our human beings.

Post-translational modifications (PTMs) of histones are hallmarks of epigenetic regulation. Studies have shown that the silencing of tumor suppressor genes by epigenetic modifiers is an early event during tumorigenesis. Over the past few decades, the approval of anticancer drugs targeting histone deacetylases and DNA methyltransferases has highlighted the important role of epigenetics in human diseases, which further suggests that factors controlling gene expression can be regarded as novel drug targets. Peptidyl arginine deiminase 4 (PAD4) is such a target, with functions in gene expression similar to those of the histone deacetylase. As a transcriptional co-regulator, the PAD4 catalyzes the calcium-dependent conversion of specific arginine residues in proteins to citrulline. In cancer, PAD4 is not only a transcriptional co-repressor of a tumor suppressor protein p53, but also participates in mediating the formation of malignant tumors. Due to a regulatory role in cell signaling pathways and disease pathogenesis, the PAD4 has become a potential therapeutic target for various diseases. Based on a small-molecule substrate N-benzoyl-L-argininamide (BAA) of the PAD4, researchers have developed a variety of potent and irreversible haloacetamidine-based PAD4 inhibitors. However, there are still problems such as unsatisfactory biological activity.

SUMMARY

An objective of the present disclosure is to provide a fluorescently-traceable amino acid derivative and a preparation method and use thereof. The fluorescently-traceable amino acid derivative has a desirable biological activity.

To achieve the above objective, the present disclosure provides the following technical solutions:

The present disclosure provides a fluorescently-traceable amino acid derivative, having a structure shown in formula I:

formula I

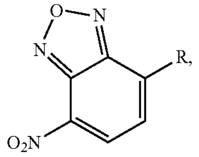

where, in formula I, R is any one of the groups shown in formula 1 to formula 10:

formula 1

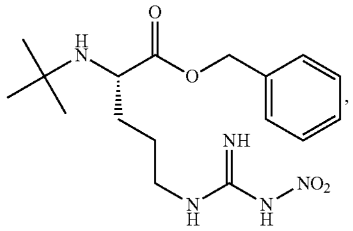

formula 2

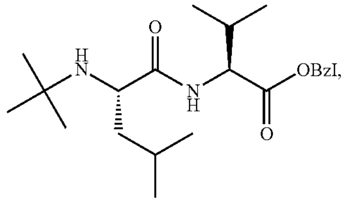

formula 3

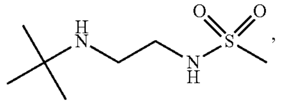

formula 4

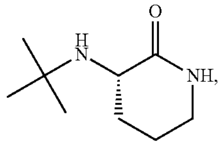

formula 5

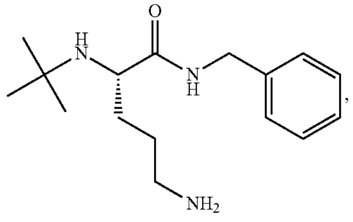

formula 6

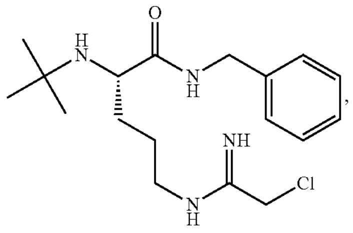

-continued formula 7

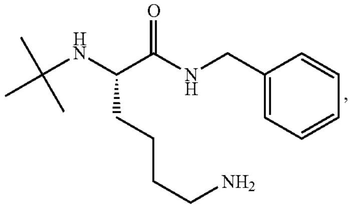

, formula 8

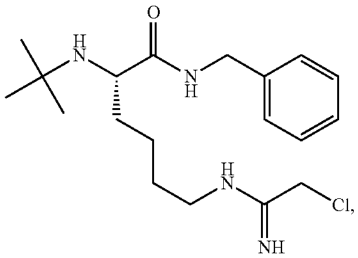

formula 9

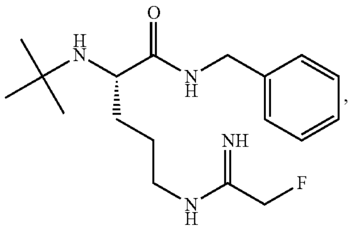

, and formula 10

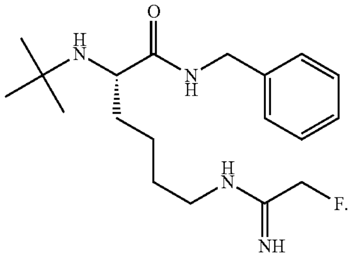

The present disclosure further provides a preparation method of the fluorescently-traceable amino acid derivative, where (i) when R is the group shown in formula 1, formula 2, or formula 3, the preparation method of the fluorescently-traceable amino acid derivative includes the following steps:

mixing 4-chloro-7-nitro-2,1,3-benzoxadiazole, methanol, and a first reaction raw material, adjusting a resulting mixed solution to a pH value of 9.5 to 10.5 with N,N-diisopropylethylamine, and conducting substitution in the dark to obtain the fluorescently-traceable amino acid derivative; where the first reaction raw material is selected from the group consisting of TosArg($NO_2$)-OBzl, HCl·LV-OBzl, and N-(2-aminoethyl)methanesulfonamide;

(ii) when R is the group shown in formula 4, the preparation method of the fluorescently-traceable amino acid derivative includes the following steps:

mixing 4-chloro-7-nitro-2,1,3-benzoxadiazole, methanol, and a second reaction raw material, adjusting a resulting mixed solution to a pH value of 9.5 to 10.5 with N,N-diisopropylethylamine, and conducting substitution in the dark to obtain a first intermediate product;

dissolving the first intermediate product in ethyl acetate, mixing a resulting mixed solution with an ethyl acetate solution of HCl, and conducting hydrolysis to obtain a second intermediate product; and dissolving the second intermediate product in methanol, adjusting a resulting mixed solution to a pH value of 9.5 to 10.5 with triethylamine, and conducting ammonia substitution in the dark to obtain the fluorescently-traceable amino acid derivative; where the second reaction raw material has a structural formula as follows:

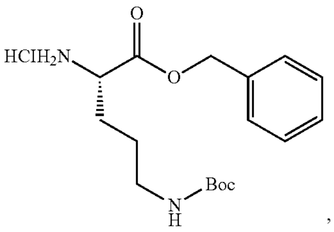

, the first intermediate product has a structural formula as follows:

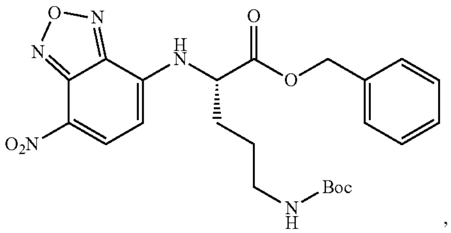 [SMILES: CC(C)(C)OC(=O)NCCC[C@H](Nc1ccc([N+](=O)[O-])c2nonc12)C(=O)OCc1ccccc1]

, the second intermediate product has a structural formula as follows:

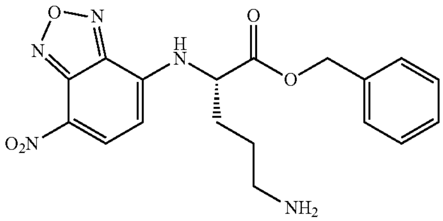

;

(iii) when R is the group shown in formula 5 or formula 7, the preparation method of the fluorescently-traceable amino acid derivative includes the following steps:

dissolving a third reaction raw material in tetrahydrofuran, mixing a resulting mixed solution I with 1-hydroxybenzotriazole and dicyclohexylcarbodiimide to conduct activation, mixing a resulting activation system with benzylamine, adjusting an obtained mixed solution II to a pH value of 8 to 9 with N-methylmorpholine, and conducting condensation to obtain a third intermediate product;

dissolving the third intermediate product in methanol, and conducting hydrogenolysis in a hydrogen atmosphere in the presence of palladium on carbon to obtain a fourth intermediate product;

dissolving the fourth intermediate product and 4-chloro-7-nitro-2,1,3-benzoxadiazole in methanol, adjusting a resulting mixed solution to a pH value of 9.5 to 10.5 with N,N-diisopropylethylamine, and conducting substitution to obtain a fifth intermediate product; and dissolving the fifth intermediate product in ethyl acetate, mixing a resulting mixed solution with an ethyl acetate solution of HCl, and conducting hydrolysis to obtain the fluorescently-traceable amino acid derivative; where the third reaction raw material has a structural formula as follows:

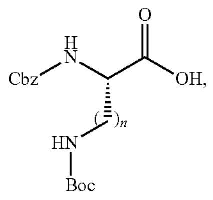

the third intermediate product has a structural formula as follows:

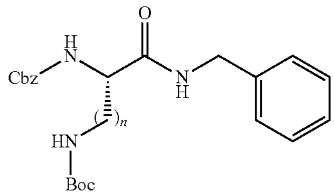
, the fourth intermediate product has a structural formula as follows:

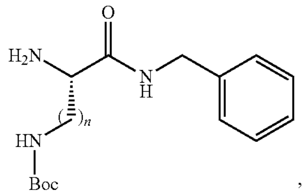
, the fifth intermediate product has a structural formula as follows:

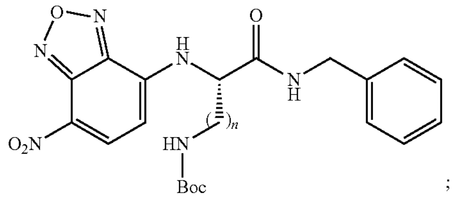
;

(iv) when R is the group shown in formula 6, formula 8, formula 9, or formula 10, the preparation method of the fluorescently-traceable amino acid derivative includes the following steps:

mixing the fourth reaction raw material, the fifth reaction raw material, and methanol, adjusting a resulting mixed solution to a pH value of 9.5 to 10.5 with N,N-diisopropylethylamine, and conducting substitution to obtain the fluorescently-traceable amino acid derivative; where the fifth reaction raw material is selected from the group consisting of ethyl 2-chloroacetimidate and ethyl 2-fluoroacetimidate, and the fourth reaction raw material has a structural formula as follows:

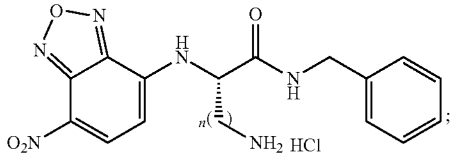
;

in the structural formulas of the third reaction raw material, the third intermediate product, the fourth intermediate product, the fifth intermediate product, and the fourth reaction raw material, n is 3 or 4.

Preferably, in (i), the substitution is conducted at 15° C. to 35° C.

Preferably, in (ii), the substitution is conducted at 15° C. to 35° C., the hydrolysis is conducted in an ice bath, and the ammonia substitution is conducted in an ice bath.

Preferably, in (iii), the condensation, the hydrogenolysis, and the substitution each are conducted at 15° C. to 35° C., and the hydrolysis is conducted in an ice bath.

Preferably, in (iv), the substitution is conducted at 15° C. to 35° C.

The present disclosure further provides a method for treating a tumor, including administrating the fluorescently-traceable amino acid derivative to a subject in need.

Preferably, the tumor includes lung cancer, colon cancer, osteosarcoma, or breast cancer.

The present disclosure provides a fluorescently-traceable amino acid derivative having a structure shown in formula I. In the present disclosure, an amino acid skeleton of the amino acid derivative is modified mainly by a fluorescently-traceable functional group. 4-chloro-7-nitro-2,1,3-benzoxadiazole (NBD-Cl) has low polarity and strong fluorescence, and can be used to modify an N-terminal of the amino acid skeleton to conduct subcellular imaging. Moreover, the NBD-Cl has a relatively small volume, lacks reaction orthogonality, and causes little interference with biochemical reactions of the organism itself. The results of examples show that the fluorescently-traceable amino acid derivative has a desirable biological activity and can be fluorescently traced in vivo and in vitro.

BRIEF DESCRIPTION OF THE DRAWINGS

FIG. 4 shows a tumor growth trend of mice injected with the compounds ZD-E-1 and ZD-F-1;

DETAILED DESCRIPTION OF THE EMBODIMENTS

Figure 1A:
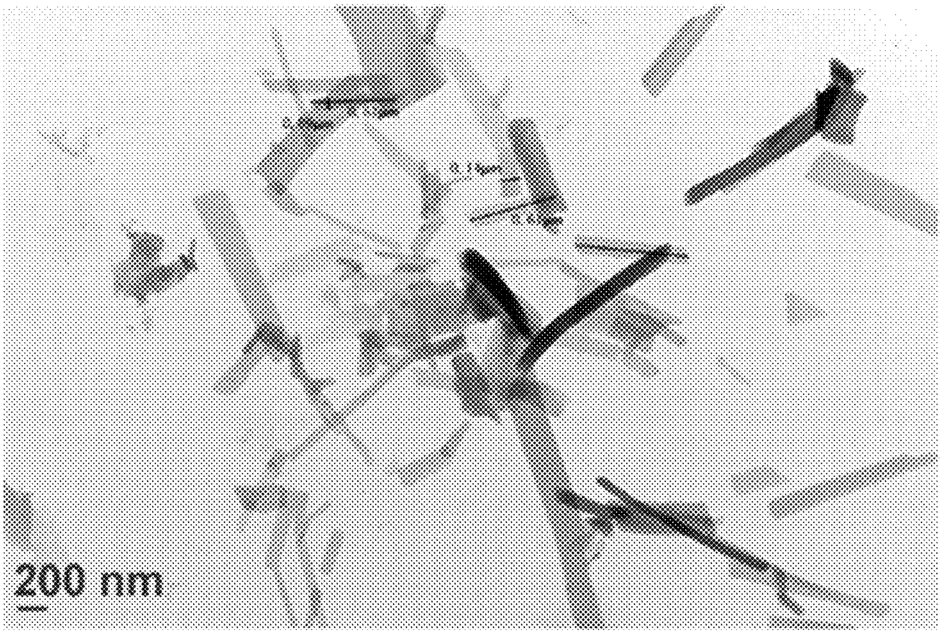
FIG. 1A-H show a transmission electron microscopy (TEM) image, a scanning electron microscopy (SEM) image, a hydration particle size variation curve, and a Zeta potential variation curve of compounds ZD-B and ZD-E-1.

The present disclosure provides a fluorescently-traceable amino acid derivative, having a structure shown in formula I:

formula I

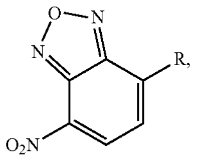

where in formula I, R is any one of the groups shown in formula 1 to formula 10:

formula 1

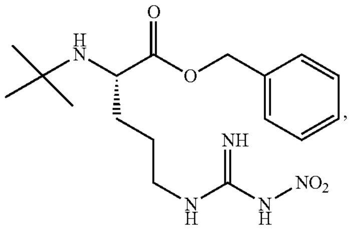

formula 2

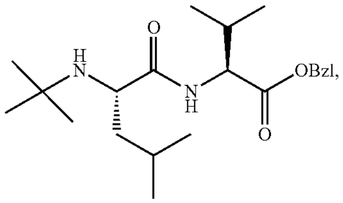

formula 3

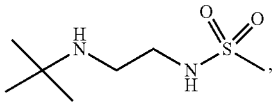

formula 4

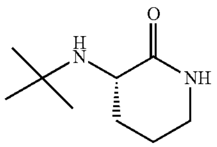

formula 5

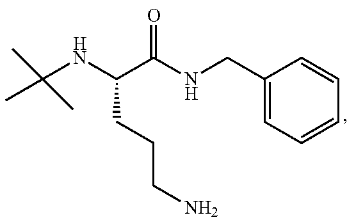

-continued formula 6

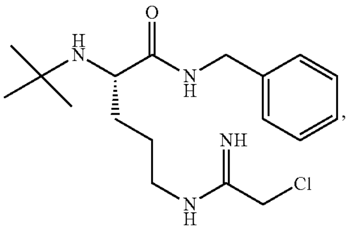

formula 7

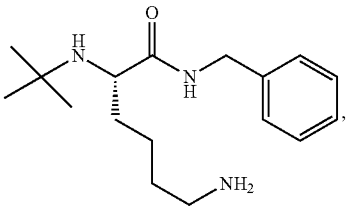

formula 8

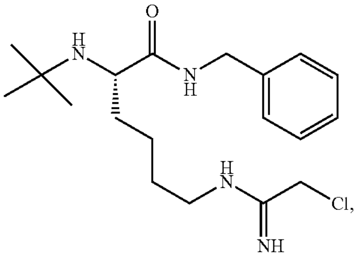

formula 9

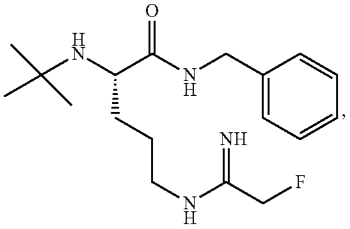

and formula 10

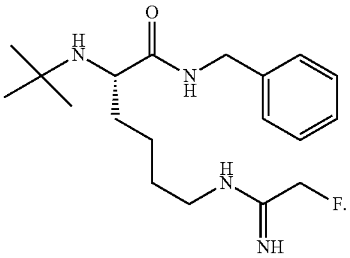

In the present disclosure, the fluorescently-traceable amino acid derivative is specifically any one selected from the group consisting of compounds shown in formula I-1 to formula I-10:

formula I-1

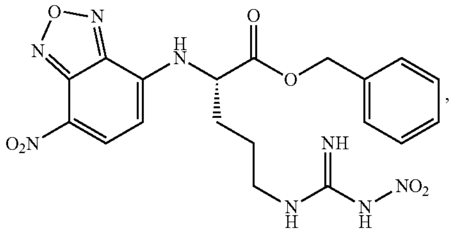

(denoted as ZD-A)

formula I-2

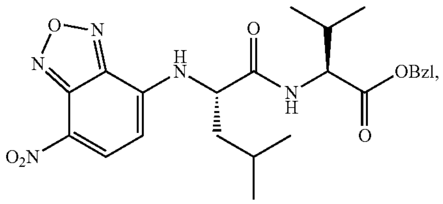

(denoted as ZD-B)

formula I-3

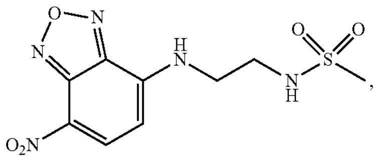

(denoted as ZD-C)

formula I-4

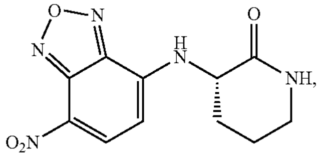

(denoted as ZD-D)

formula I-5

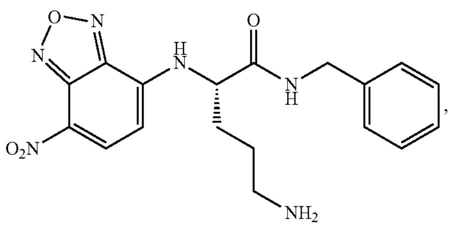

(denoted as ZD-E)

formula I-6

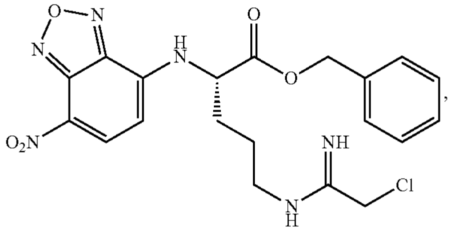

(denoted as ZD-E-1)

-continued formula I-7

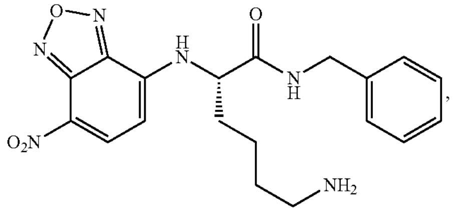

(denoted as ZD-F)

formula I-8

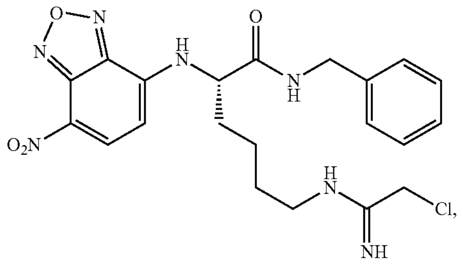

(denoted as ZD-F-1)

formula I-9

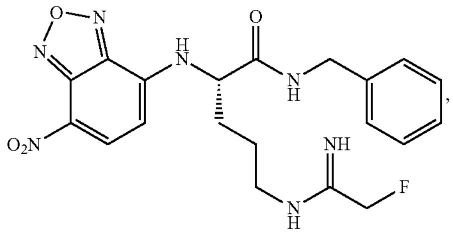

(denoted as ZD-E-2)

formula I-10

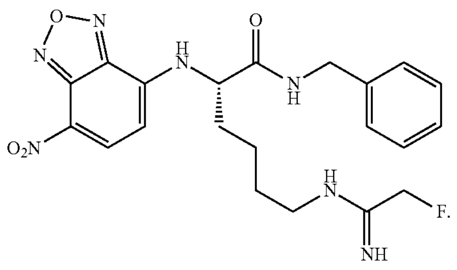

(denoted as ZD-F-2)

The present disclosure provides a preparation method of the fluorescently-traceable amino acid derivative. In the present disclosure, different preparation methods are preferably adopted according to a type of R in the fluorescently-traceable amino acid derivative, which will be described in detail below.

In the present disclosure, unless otherwise specified, all raw materials required for preparation are commercially available products well known to persons skilled in the art.

In the present disclosure, when R is the group shown in formula 1, formula 2, or formula 3, the preparation method of the fluorescently-traceable amino acid derivative includes the following steps:

mixing 4-chloro-7-nitro-2,1,3-benzoxadiazole, methanol, and a first reaction raw material, adjusting a resulting mixed solution to a pH value of 9.5 to 10.5 with N,N-diisopropylethylamine, and conducting substitution in the dark to obtain the fluorescently-traceable amino acid derivative; where the first reaction raw material is selected from the group consisting of Tos·Arg($NO_2$)-OBzl, HCl·LV-OBzl, and N-(2-aminoethyl)methanesulfonamide;

A reaction route is as follows:

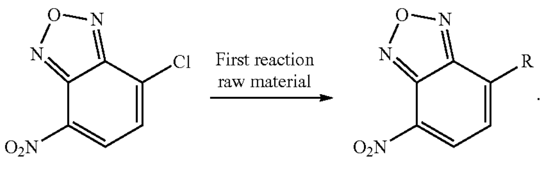

In the present disclosure, the 4-chloro-7-nitro-2,1,3-benzoxadiazole (NBD-Cl) and the first reaction raw material are at a molar ratio of preferably 5:6; the NBD-Cl and the methanol are at a dosage ratio of preferably 5 mmol:(90-110) mL, more preferably 5 mmol: 100 mL. Preferably, the NBD-Cl is dissolved in the methanol, the first reaction raw material is added to a resulting NBD-Cl methanol solution under stirring in an ice bath (0° C.), a resulting mixed solution is adjusted to a pH value of 9.5 to 10.5 with N,N-diisopropylethylamine (DIPEA), the ice bath is removed, and substitution is conducted in the dark. The pH value of the resulting mixed solution is preferably adjusted to 10 using the DIPEA.

In the present disclosure, the substitution is conducted at preferably 15° C. to 35° C., more preferably 20° C. to 30° C.; preferably the substitution is conducted at a room temperature, without additional heating or cooling; in the examples, the substitution is specifically conducted at 25° C. Preferably, the substitution is monitored by TLC, and after the NBD-Cl raw material is observed to disappear, it is determined that the substitution is complete; according to a volume ratio, a developer for the TLC monitoring is preferably a mixture of petroleum ether (PE):ethyl acetate (EA)=(1-2):1.

In the present disclosure, after the substitution is completed, an obtained system is preferably separated and purified through a medium-pressure preparative column; a purification reagent is a mixture of EA and PE, where the EA is at a volume fraction of 35% to 50%; an obtained purified product is dissolved in methanol, then ultrasonicated; a solid is precipitated after standing still, and then subjected to filtration under reduced pressure to obtain a solid material, namely the fluorescently-traceable amino acid derivative.

In the present disclosure, there is no special limitation on a source of the first reaction raw material, which can be commercially available products or prepared by well-known methods known to those skilled in the art. In the present disclosure, the Tos·Arg($NO_2$)-OBzl and N-(2-aminoethyl) methanesulfonamide are specifically commercially available products; the HCl·LV-OBzl is preferably prepared according to methods well known to those skilled in the art. A reaction route is as follows (an example of a specific preparation method is described in detail in Example 2 of the present disclosure):

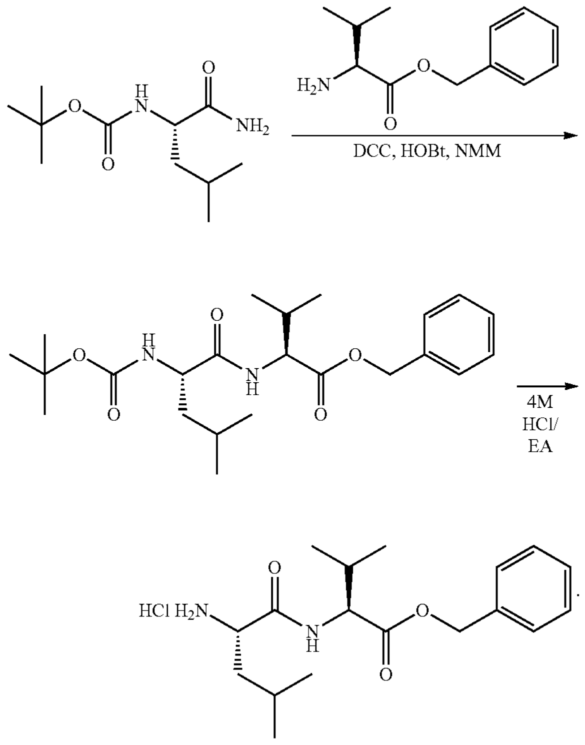

In the present disclosure, when R is the group shown in formula 4, the preparation method of the fluorescently-traceable amino acid derivative includes the following steps:

mixing 4-chloro-7-nitro-2,1,3-benzoxadiazole, methanol, and a second reaction raw material, adjusting a resulting mixed solution to a pH value of 9.5 to 10.5 with N,N-diisopropylethylamine (DIPEA), and conducting substitution in the dark to obtain a first intermediate product;

dissolving the first intermediate product in ethyl acetate, mixing a resulting mixed solution with an ethyl acetate solution of HCl, and conducting hydrolysis to obtain a second intermediate product; and dissolving the second intermediate product in methanol, adjusting a resulting mixed solution to a pH value of 9.5 to 10.5 with triethylamine, and conducting ammonia substitution in the dark to obtain the fluorescently-traceable amino acid derivative; where the second reaction raw material has a structural formula as follows:

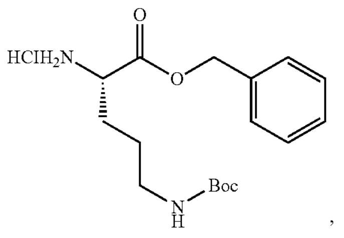

the first intermediate product has a structural formula as follows:

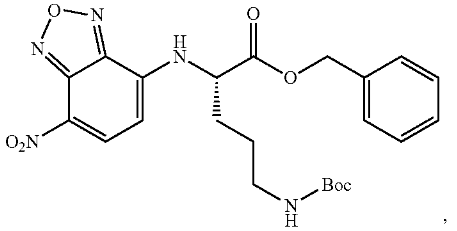 [SMILES: CC(C)(C)OC(=O)NCCC[C@H](Nc1ccc([N+](=O)[O-])c2nonc12)C(=O)OCc1ccccc1]
, the second intermediate product has a structural formula as follows:

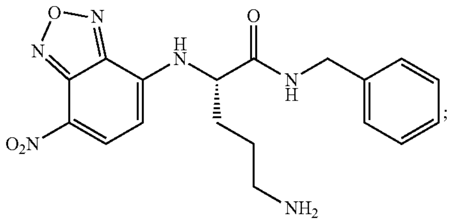 [SMILES: NCCC[C@H](Nc1ccc([N+](=O)[O-])c2nonc12)C(=O)NCc1ccccc1]
;

A reaction route is as follows:

9.5 to 10.5 with N,N-diisopropylethylamine (DIPEA), the ice bath is removed, and substitution is conducted in the dark. The pH value of the resulting mixed solution is preferably adjusted to 10 using the DIPEA.

In the present disclosure, the substitution is conducted at preferably 15° C. to 35° C., more preferably 20° C. to 30° C.; the substitution is preferably conducted at a room temperature. Preferably, the substitution is monitored by TLC, and after the NBD-Cl raw material is observed to disappear, it is determined that the substitution is complete; according to a volume ratio, a developer for the TLC monitoring is preferably a mixture of PE:EA=2:1.

In the present disclosure, after the substitution is completed, an obtained system is preferably separated and purified through a medium-pressure preparative column; a purification reagent is a mixture of EA and PE, where the EA is at a volume fraction of 35%; and the first intermediate product (NBD-Orn(Boc)-OBzl) is obtained.

In the present disclosure, the first intermediate product is dissolved in ethyl acetate, a resulting mixed solution is mixed with an ethyl acetate solution of HCl, and hydrolysis is conducted to obtain a second intermediate product. After the first intermediate product is dissolved in ethyl acetate, the resulting mixed solution has preferably 0.35 mol/L to 0.45 mol/L, more preferably 0.4 mol/L of the first interme-

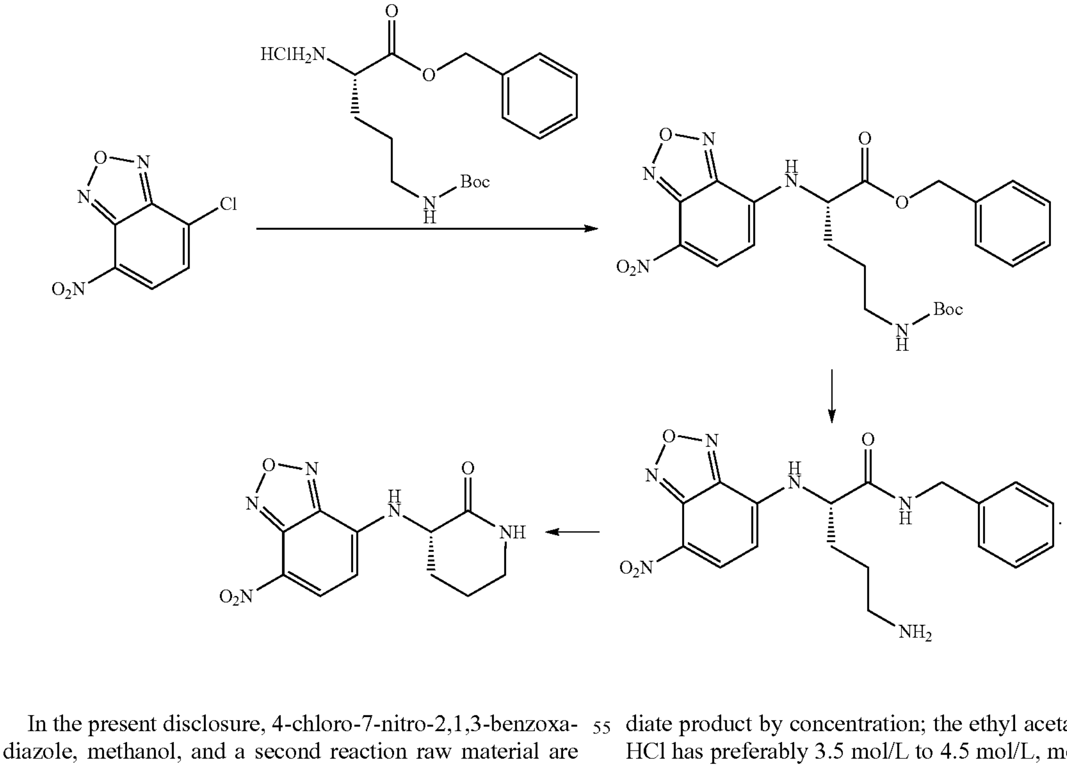
.

In the present disclosure, 4-chloro-7-nitro-2,1,3-benzoxadiazole, methanol, and a second reaction raw material are mixed, a resulting mixed solution is adjusted to a pH value of 9.5 to 10.5 with N,N-diisopropylethylamine (DIPEA), and substitution is conducted in the dark to obtain a first intermediate product. The NBD-Cl and the second reaction raw material (HCl·Orn(Boc)-OBzl) are at a molar ratio of preferably 5:6; the NBD-Cl and the methanol are at a dosage ratio of preferably 5 mmol:(90-110) mL, more preferably 5 mmol: 100 mL. Preferably, the NBD-Cl is dissolved in the methanol, the second reaction raw material is added to a resulting NBD-Cl methanol solution under stirring in an ice bath, a resulting mixed solution is adjusted to a pH value of diate product by concentration; the ethyl acetate solution of HCl has preferably 3.5 mol/L to 4.5 mol/L, more preferably 4 mol/L of the HCl by concentration; the mixed solution and the ethyl acetate solution of HCl (referred to as a HCl/EA solution) are at a volume ratio of preferably 1:2.

In the present disclosure, preferably, the first intermediate product is dissolved in ethyl acetate; in a fume hood, the HCl/EA solution is added to the resulting mixed solution under stirring in an ice bath; and the hydrolysis is conducted under stirring in an ice bath. Preferably, the hydrolysis is monitored by TLC, and after the first intermediate product raw material is observed to disappear, it is determined that the hydrolysis is complete; according to a volume ratio, a developer for the TLC monitoring is preferably a mixture of EA:$H_2O$:glacial acetic acid (HAc)=6:1:1.

In the present disclosure, after the hydrolysis is completed, an obtained system is preferably vacuum-dried under stirring in a warm water bath at 37° C., and a residue is reconstituted with dry EA and then vacuum-dried again; the above operations are repeated 3 times until there is no obvious acid gas residue, so as to obtain the second intermediate product.

In the present disclosure, the second intermediate product is dissolved in methanol, a resulting mixed solution is adjusted to a pH value of 9.5 to 10.5 with triethylamine, and ammonia substitution is conducted in the dark to obtain the fluorescently-traceable amino acid derivative. Preferably, the second intermediate product is dissolved in the methanol, and the pH value of the resulting mixed solution is adjusted to 9.5 to 10.5 (preferably 10) with the triethylamine under stirring in an ice bath, and the ammonia substitution is conducted in the dark. Preferably, the ammonia substitution is monitored by TLC, and after the second intermediate product raw material is observed to disappear, it is determined that the ammonia substitution is complete; according to a volume ratio, a developer for the TLC monitoring is preferably a mixture of PE:EA=2:1.

In the present disclosure, after the ammonia substitution is completed, an obtained system is preferably separated and purified through a medium-pressure preparative column; a purification reagent is a mixture of EA and PE, where the EA is at a volume fraction of 32%; and the fluorescently-traceable amino acid derivative is obtained.

In the present disclosure, when R is the group shown in formula 5 or formula 7, the preparation method of the fluorescently-traceable amino acid derivative includes the following steps:

dissolving a third reaction raw material in tetrahydrofuran, mixing a resulting mixed solution I with 1-hydroxybenzotriazole and dicyclohexylcarbodiimide to conduct activation, mixing a resulting activation system with benzylamine, adjusting an obtained mixed solution II to a pH value of 8 to 9 with N-methylmorpholine, and conducting condensation to obtain a third intermediate product;

dissolving the third intermediate product in methanol, and conducting hydrogenolysis in a hydrogen atmosphere in the presence of palladium on carbon to obtain a fourth intermediate product;

dissolving the fourth intermediate product and 4-chloro-7-nitro-2,1,3-benzoxadiazole in methanol, adjusting a resulting mixed solution to a pH value of 9.5 to 10.5 with N,N-diisopropylethylamine (DIPEA), and conducting substitution to obtain a fifth intermediate product; and dissolving the fifth intermediate product in ethyl acetate, mixing a resulting mixed solution with an ethyl acetate solution of HCl, and conducting hydrolysis to obtain the fluorescently-traceable amino acid derivative; where the third reaction raw material has a structural formula as follows:

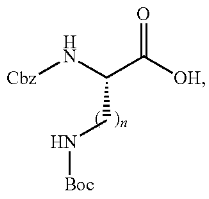

, the third intermediate product has a structural formula as follows:

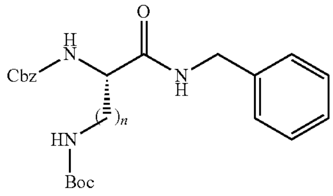

, the fourth intermediate product has a structural formula as follows:

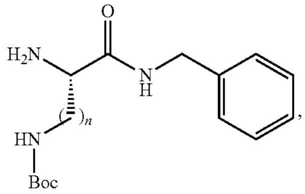

, the fifth intermediate product has a structural formula as follows:

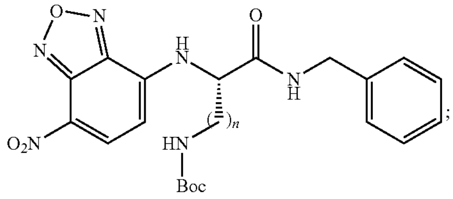

;

in the structural formulas of the third reaction raw material, the third intermediate product, the fourth intermediate product, and the fifth intermediate product, n is 3 or 4;

A reaction route is as follows (a product is represented as hydrochloride):

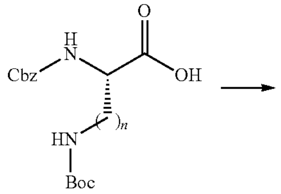

-continued

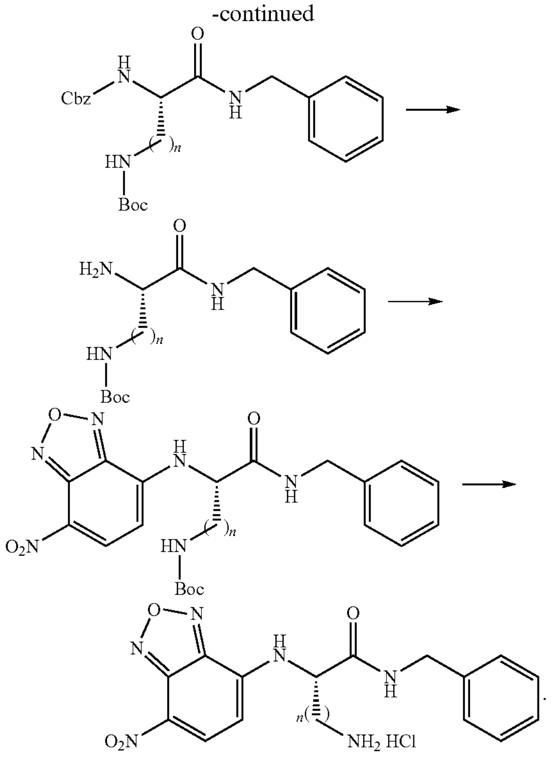

In the present disclosure, when n is preferably 3, the fluorescently-traceable amino acid derivative has the structure shown in formula 1-5; when n is preferably 4, the fluorescently-traceable amino acid derivative has the structure shown in formula 1-7.

In the present disclosure, a third reaction raw material is dissolved in tetrahydrofuran, a resulting mixed solution I is mixed with 1-hydroxybenzotriazole and dicyclohexylcarbodiimide to conduct activation, a resulting activation system is mixed with benzylamine, an obtained mixed solution II is adjusted to a pH value of 8 to 9 with N-methylmorpholine, and condensation is conducted to obtain a third intermediate product. The third reaction raw material and the tetrahydrofuran (THF) are at a dosage ratio of preferably 1 mmol:(9-11) mL, more preferably 1 mmol: 10 mL; the third reaction raw material, the 1-hydroxybenzotriazole (HOBt), and the dicyclohexylcarbodiimide (DCC) are at a molar ratio of preferably 10:(11-13):(11-13), more preferably 10:12:12; and the third reaction raw material and the benzylamine are at a dosage ratio of preferably 10 mmol:(1.6-5.6) mL.

In the present disclosure, preferably, the third reaction raw material is dissolved in the tetrahydrofuran, and the 1-hydroxybenzotriazole and the dicyclohexylcarbodiimide are added to an obtained mixed solution under stirring in an ice bath to conduct activation for 8 min to 12 min, preferably 10 min, and a white solid precipitates out; the benzylamine is added to an obtained activation system, an obtained mixed solution is adjusted to a pH value of 8 to 9 with the N-methylmorpholine (NMM), and the ice bath is removed to conduct the condensation. The condensation is conducted at preferably 15° C. to 35° C., more preferably 20° C. to 30° C.; the condensation is conducted preferably at a room temperature. Preferably, the condensation is monitored by TLC, and after the third reaction raw material is observed to disappear, it is determined that the condensation is complete; according to a volume ratio, a developer for the TLC monitoring is preferably a mixture of dichloromethane: methanol=30:1.

In the present disclosure, after the condensation is completed, an obtained system is preferably filtered under reduced pressure, THF in a filtrate is removed, and ethyl acetate is added to a residue; an obtained system is sequentially washed with a saturated $NaHCO_3$ solution, a saturated NaCl solution, a 5 wt % $KHSO_4$ solution, the saturated NaCl solution, a 5 wt % $NaHCO_3$ solution, and the saturated NaCl solution, and then dried with anhydrous $Na_2SO_4$; after drying, the $Na_2SO_4$ is removed by normal-pressure filtration, and a resulting filtrate is concentrated under reduced pressure to obtain a colorless oil; the colorless oil is separated and purified through a medium-pressure preparative column; according to a volume ratio, a reagent for collecting a product is a mixture of dichloromethane:methanol=95:5; and the third intermediate product is obtained.

In the present disclosure, the third intermediate product is dissolved in methanol, and hydrogenolysis is conducted in a hydrogen atmosphere in the presence of palladium on carbon to obtain a fourth intermediate product. The third intermediate product and the methanol are at a dosage ratio of preferably (5-10) mmol:(40-50) mL; the palladium on carbon is used as a catalyst, with a dosage that can ensure a smooth progress of the hydrogenolysis. The hydrogenolysis is conducted at preferably 15° C. to 35° C., more preferably 20° C. to 30° C.; the hydrogenolysis is conducted preferably at a room temperature. Preferably, the hydrogenolysis is monitored by TLC, and after the third intermediate product raw material is observed to disappear, it is determined that the hydrogenolysis is complete; according to a volume ratio, a developer for the TLC monitoring is preferably a mixture of dichloromethane:methanol=10:1.

In the present disclosure, after the hydrogenolysis is completed, an obtained system is preferably filtered under a normal pressure, the palladium on carbon is removed, and the solvent in the filtrate is removed to obtain the fourth intermediate product.

In the present disclosure, the fourth intermediate product and 4-chloro-7-nitro-2,1,3-benzoxadiazole are dissolved in methanol, a resulting mixed solution is adjusted to a pH value of 9.5 to 10.5 with N,N-diisopropylethylamine (DIPEA), and substitution is conducted to obtain a fifth intermediate product. The NBD-Cl and the fourth intermediate product are at a molar ratio of preferably 5:6; the NBD-Cl and the methanol are at a dosage ratio of preferably 5 mmol:(40-100) mL.

In the present disclosure, preferably the NBD-Cl and the fourth intermediate product are dissolved in the methanol, and an obtained system is adjusted to a pH value of 9.5 to 10.5 with the DIPEA under stirring in an ice bath; the ice bath is removed to conduct the substitution; the pH value of the resulting mixed solution is preferably adjusted to 10 with the DIPEA. In the present disclosure, the substitution is conducted at preferably 15° C. to 35° C., more preferably 20° C. to 30° C.; the substitution is preferably conducted at a room temperature. Preferably, the substitution is monitored by TLC, and after the NBD-Cl raw material is observed to disappear, it is determined that the substitution is complete; according to a volume ratio, a developer for the TLC monitoring is preferably a mixture of petroleum ether:ethyl acetate=2:1.

In the present disclosure, after the substitution is completed, an obtained system is preferably spin-dried under reduced pressure, and an obtained residue is separated and purified through a medium-pressure preparative column; a purification reagent is a mixture of EA and PE, where the EA is at a volume fraction of 35%; and the fifth intermediate product is obtained.

In the present disclosure, the fifth intermediate product is dissolved in ethyl acetate, a resulting mixed solution is mixed with an ethyl acetate solution of HCl, and hydrolysis is conducted to obtain the fluorescently-traceable amino acid derivative. After the fifth intermediate product is dissolved in ethyl acetate, the resulting mixed solution has preferably 0.5 mol/L to 0.6 mol/L of the fifth intermediate product by concentration; the ethyl acetate solution of HCl has preferably 2 mol/L to 4 mol/L of the HCl by concentration; the mixed solution and the ethyl acetate solution of HCl (referred to as a HCl/EA solution) are at a volume ratio of preferably 1:(2-3).

In the present disclosure, preferably, the fifth intermediate product is dissolved in ethyl acetate; in a fume hood, the HCl/EA solution is added to the resulting mixed solution under stirring in an ice bath; and the hydrolysis is conducted under stirring in an ice bath. Preferably, the hydrolysis is monitored by TLC, and after the fifth intermediate product raw material is observed to disappear, it is determined that the hydrolysis is complete; according to a volume ratio, a developer for the TLC monitoring is preferably a mixture of EA:$H_2O$:HAc=6:1:1.

In the present disclosure, after the hydrolysis is completed, an obtained system is preferably subjected to suction filtration to remove the solvent, and an obtained residue is sequentially subjected to suction filtration and washed with ethyl acetate and diethyl ether to obtain the fluorescently-traceable amino acid derivative (in the form of a hydrochloride).

In the present disclosure, when R is the group shown in formula 6, formula 8, formula 9, or formula 10, the preparation method of the fluorescently-traceable amino acid derivative includes the following steps:

mixing the fourth reaction raw material, the fifth reaction raw material, and methanol, adjusting a resulting mixed solution to a pH value of 9.5 to 10.5 with N,N-diisopropylethylamine (DIPEA), and conducting substitution to obtain the fluorescently-traceable amino acid derivative; where the fifth reaction raw material is selected from the group consisting of ethyl 2-chloroacetimidate and ethyl 2-fluoroacetimidate, and the fourth reaction raw material has a structural formula as follows:

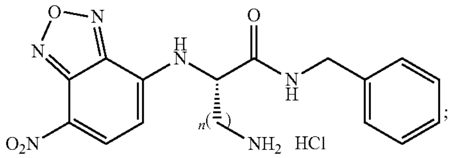

;

in the structural formula of the fourth reaction raw material, n is 3 or 4;

A reaction route is as follows:

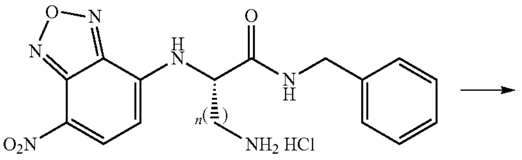

-continued

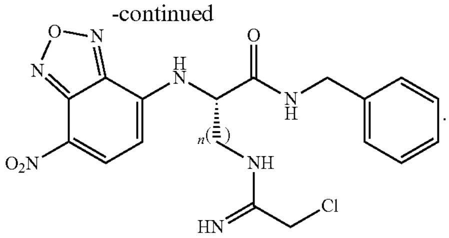

.

In the present disclosure, when n is preferably 3, the fluorescently-traceable amino acid derivative has the structure shown in formula 1-6 or formula 1-9; when n is preferably 4, the fluorescently-traceable amino acid derivative has the structure shown in formula 1-8 or formula I-10.

In the present disclosure, specifically, when R is the group shown in formula 6 or formula 8, the fifth reaction raw material is ethyl 2-chloroacetimidate; when R is the group shown in formula 9 or formula 10, the fifth reaction raw material is ethyl 2-fluoroacetimidate.

In the present disclosure, the fourth reaction raw material and the fifth reaction raw material are at a molar ratio of preferably 1:(1-2); and the fourth reaction raw material and the methanol are at a dosage ratio of preferably (1-3) mmol:(40-50) mL. Preferably, the fourth reaction raw material is dissolved in the methanol, and the fifth reaction raw material is added to a resulting mixed solution under stirring in an ice bath; an obtained system is adjusted to a pH value of 9.5 to 10.5 with DIPEA, and the ice bath is removed to conduct the substitution. The pH value of the resulting mixed solution is preferably adjusted to 10 using the DIPEA.

In the present disclosure, the substitution is conducted at preferably 15° C. to 35° C., more preferably 20° C. to 30° C.; the substitution is preferably conducted at a room temperature. Preferably, the substitution is monitored by TLC, and after the fourth reaction raw material is observed to disappear, it is determined that the substitution is complete; according to a volume ratio, a developer for the TLC monitoring is preferably a mixture of EA:$H_2O$:HAc=6:1:1.

In the present disclosure, after the substitution is completed, an obtained system is preferably spin-dried to remove the solvent, a residue is re-dissolved with a 5% methanol aqueous solution by volume fraction, and then separated and purified by C18 silica gel column chromatography using a methanol aqueous solution with a volume fraction of 40% to 60%, spin-dried to remove the methanol, and freeze-dried to remove water, so as to obtain the fluorescently-traceable amino acid derivative.

The present disclosure further provides a method for treating a tumor, including administrating the fluorescently-traceable amino acid derivative to a subject in need. In the present disclosure, the tumor includes preferably lung cancer, colon cancer, osteosarcoma, or breast cancer. The antitumor drug includes the fluorescently-traceable amino acid derivative and a pharmaceutically acceptable auxiliary material; the antitumor drug has preferably 20 wt. % to 80 wt. % of the fluorescently-traceable amino acid derivative; the pharmaceutically acceptable auxiliary material is preferably one or more selected from the group consisting of cyclodextrin, 2-hydroxypropyl-β-cyclodextrin, and mannitol; and a dosage form of the antitumor drug includes preferably a lyophilized powder, a nanoemulsion, or a liposome.

The technical solutions of the present disclosure will be clearly and completely described below with reference to the examples of the present disclosure. Apparently, the described examples are only a part of, not all of, the examples of the present disclosure. All other examples obtained by a person of ordinary skill in the art based on the examples of the present disclosure without creative efforts shall fall within the protection scope of the present disclosure.

Example 1

Synthesis of NBD-Arg($NO_2$)-OBzl (ZD-A)

0.998 g (5 mmol) of 4-chloro-7-nitro-2,1,3-benzoxadiazole (NBD-Cl) was added in an eggplant-shaped flask by weight reduction, and dissolved with 100 mL of anhydrous methanol to obtain a yellow, clear, and transparent solution, and a stirring bar was added; 1.85 g (6 mmol) of Tos·Arg ($NO_2$)-OBzl under ice-bath stirring, and an obtained mixed solution was adjusted to a pH value of 10 with 2.6 mL of N,N-diisopropylethylamine (DIPEA); the ice bath was removed, and reaction was conducted in the dark at a room temperature (25° C.) for 8 h, and it was observed that the color of a reaction solution gradually deepened to dark green, accompanied by green fluorescence; the reaction progress was monitored by TLC (according to a volume ratio, a developer was a mixture of PE:EA=1:1, $R_f$=0.25), and the reaction was determined to be complete after the disappearance of the NBD-Cl raw material was observed. After the reaction, an obtained system was separated and purified by a medium-pressure preparative column (a purification reagent was a mixture of EA and PE, where a volume fraction of the EA was 50%), and dissolved in 2 mL of methanol and ultrasonicated; a solid was precipitated after standing still, and then filtered under reduced pressure to obtain 610 mg (26.8%) of a target product ZD-A as a yellow solid powder, with bright green fluorescence in an organic solvent. M.p.: 166.0-168.8° C.;

$$[\alpha]_D^{25} = -20.2,$$

(C=0.1, $CH_3OH$); ESI-MS (m/z): 471.3 $[M-H]^-$; 1H-NMR (300 MHz, DMSO-$d_6$): δ (ppm)=9.50 (d, J=6.7 Hz, 1H), 8.53 (s, 1H), 8.50 (s, 1H), 8.00 (s, 1H), 7.85 (s, 1H), 7.32 (s, 5H), 6.41 (s, 1H), 5.18 (s, 2H), 4.76 (s, 1H), 3.19 (dt, J=6.8 Hz, 6.2 Hz, 2H), 2.04 (m, 2H), 1.65 (m, 2H); 13C-NMR (75 MHz, DMSO-$d_6$): δ/ppm=171.0, 159.8, 144.6, 137.8, 136.0, 128.9, 128.6, 128.4, 100.7, 67.1, 56.4, 28.4, 25.3.

Example 2

Synthesis of Boc-LV-OBzl 2.31 g (10 mmol) of Boc-Leu (tert-butoxycarbonyl leucine) was added into an eggplant-shaped flask by weight reduction, and dissolved with 150 mL of anhydrous tetrahydrofuran (THF) to obtain a colorless, clear, and transparent solution, and a stirring bar was added; under stirring in an ice bath, 1.62 g (12 mmol) of 1-hydroxybenzotriazole (HOBt) and 2.47 g (12 mmol) of dicyclohexylcarbodiimide (DCC) were sequentially added, and after activation for 30 min, there was white solid precipitated; 2.92 g (11 mmol) of HCl Val-OBzl was added to the eggplant-shaped flask, and a mixed solution was adjusted to a pH value of 8 with N-methylmorpholine (NMM); the ice bath was removed, and a reaction was conducted for 8 h by stirring at a room temperature; the progress of the reaction was monitored by TLC (according to a volume ratio, a developer was a mixture of $CH_2Cl_2$:$CH_3OH$=30:1, $R_f$=0.38), and the reaction was determined to be complete after the disappearance of the Boc-Leu raw material was observed. After the reaction, a product was filtered under reduced pressure with a vacuum circulating water pump, a filter cake was rinsed with EA, and a filtrate was concentrated to dryness under reduced pressure to remove THF; a residue was dissolved with 150 mL of EA, the solid material was removed by suction filtration, and a resulting filtrate was transferred to a 250 mL separatory funnel; the filtrate was sequentially subjected to extraction and washing with a saturated $NaHCO_3$ solution 3 times (30 mL/time), a saturated NaCl solution 3 times (30 mL/time), a 5 wt % $KHSO_4$ solution 3 times (30 mL/time), a saturated NaCl solution 3 times (30 mL/time), a saturated $NaHCO_3$ solution 3 times (30 mL/time), and a saturated NaCl solution 3 times (30 mL/time), and it was observed that the color of the EA layer became light to colorless during the extraction and washing; after the EA layer was dried with anhydrous $Na_2SO_4$ for 2 h, the $Na_2SO_4$ was removed by filtration, and a filtrate was concentrated under reduced pressure to obtain a colorless oil; the colorless oil was separated and purified by a medium-pressure preparative column (a purification reagent was a mixture of methanol and dichloromethane, and a volume fraction of the methanol was 5%) to obtain 3.68 g (87.6%) of a target product Boc-LV-OBzl, as a white solid powder. ESI-MS (m/z): 421 $[M+H]^+$.

Synthesis of HCl·LV-OBzl 1.26 g (3 mmol) of the Boc-LV-OBzl was placed in an eggplant-shaped flask and dissolved with 5 mL of dry EA. In a fume hood, 10 mL of an ethyl acetate solution of HCl (referred to as a HCl/EA solution, a concentration of HCl was 4 mol/L) was added dropwise to a resulting solution under stirring in an ice bath; a mouth of the flask was connected with a drying tube, and the solution was reacted for 3 h under stirring in an ice bath, and it was observed that an orange-red solid gradually precipitated along a wall of the flask; the progress of the reaction was monitored by TLC (according to a volume ratio, a developer was a mixture of $CH_2Cl_2$:$CH_3OH$=10:1, $R_f$=0.30), and the reaction was determined to be complete after the disappearance of the Boc-LV-OBzl raw material was observed. After the reaction was completed, under stirring in a warm water bath at 37° C., the eggplant-shaped flask was connected with a single pass having a plug, and the reaction solution was drained under reduced pressure with a vacuum circulating water pump, and a residue was reconstituted with 20 mL of the dry EA and then drained again; the above operations were repeated 3 times until there was no obvious acid gas residue, and anhydrous diethyl ether was added for grinding, washing, and drying to obtain 990 mg (92.5%) of a target product HCl·LV-OBzl as a white solid powder. ESI-MS (m/z): 3201$[M+H]^+$.

Synthesis of NBD-LV-OBzl (ZD-B)

0.998 g (5 mmol) of 4-chloro-7-nitro-2,1,3-benzoxadiazole (NBD-Cl) was added in an eggplant-shaped flask by weight reduction, and dissolved with 100 mL of anhydrous methanol to obtain a yellow, clear, and transparent solution, and a stirring bar was added; 2.14 g (6 mmol) of HCl·LV-OBzl was added under ice-bath stirring, and an obtained mixed solution was adjusted to a pH value of 10 with 2.6 mL of DIPEA; the ice bath was removed, and reaction was conducted in the dark at a room temperature for 8 h, and it was observed that the color of a reaction solution gradually deepened to dark green, accompanied by green fluorescence; the reaction progress was monitored by TLC (according to a volume ratio, a developer was a mixture of PE:EA=1:1, $R_f$=0.28), and the reaction was determined to be complete after the disappearance of the NBD-Cl raw material was observed. After the reaction, an obtained system was separated and purified by a medium-pressure preparative column (a purification reagent was a mixture of EA and PE, where a volume fraction of the EA was 50%), and dissolved in 2 mL of methanol and ultrasonicated; a solid was precipitated after standing still, and then filtered under reduced pressure to obtain 750 mg (32.1%) of a target product ZD-B as a yellow solid powder, with bright green fluorescence in an organic solvent. M.p.: 147.4-149.1° C.;

$$[\alpha]_D^{25} = -77.5,$$

(C=0.1, $CH_3OH$); ESI-MS (m/z): 482.5 $[M-H]^-$; 1H-NMR (300 MHz, DMSO-$d_6$): δ (ppm)=9.38 (s, 1H), 8.58 (s, 1H), 8.52 (d, J=8.9 Hz, 1H), 7.34 (s, 5H), 6.42 (s, 1H), 5.12 (d, J=4.1 Hz, 2H), 4.52 (s, 1H), 4.27 (t, J=6.4 Hz, 1H), 2.11 (m, 1H), 1.91 (s, 1H), 1.67 (d, J=32.0 Hz, 2H), 0.91 (t, J=5.7 Hz, 6H), 0.86 (d, J=6.3 Hz, 6H); 13C-NMR (75 MHz, DMSO-$d_6$): δ/ppm=171.4, 144.7, 137.9, 136.2, 128.8, 128.6, 128.5, 122.3, 100.1, 66.5, 58.0, 56.2, 30.3, 24.8, 23.3, 22.0, 19.4, 18.6.

Example 3

Synthesis of NBD-N-(2-aminoethyl)methanesulfonamide (ZD-C)

0.998 g (5 mmol) of NBD-Cl was added in an eggplant-shaped flask by weight reduction, and dissolved with 100 mL of anhydrous methanol to obtain a yellow, clear, and transparent solution, and a stirring bar was added; 834 mg (6 mmol) of N-(2-aminoethyl)methanesulfonamide was added under ice-bath stirring, and an obtained mixed solution was adjusted to a pH value of 10 with 2.6 mL of DIPEA; the ice bath was removed, and reaction was conducted in the dark at a room temperature for 8 h, and it was observed that the color of a reaction solution gradually deepened to dark green, accompanied by green fluorescence; the reaction progress was monitored by TLC (according to a volume ratio, a developer was a mixture of PE:EA=2:1, $R_f$=0.30), and the reaction was determined to be complete after the disappearance of the NBD-Cl raw material was observed. After the reaction, an obtained system was separated and purified by a medium-pressure preparative column (a purification reagent was a mixture of EA and PE, where a volume fraction of the EA was 35%), and dissolved in 2 mL of methanol and ultrasonicated; a solid was precipitated after standing still, and then filtered under reduced pressure to obtain 697 mg (46.3%) of a target product ZD-C as an orange-red solid powder, with bright green fluorescence in an organic solvent. M.p.: 198.8-203.5° C.;

$$[\alpha]_D^{25} = \pm 12.4,$$

(C=0.1, $CH_3OH$); ESI-MS (m/z): 300.1 $[M-H]^-$; 1H-NMR (300 MHz, DMSO-$d_6$): δ (ppm)=9.40 (s, 1H), 8.55 (d, J=8.8 Hz, 1H), 7.26 (t, J=5.7 Hz, 1H), 6.46 (d, J=8.9 Hz, 1H), 3.62 (s, 2H), 3.29 (q, J=6.1 Hz, 2H), 2.94 (s, 3H).

Example 4

Synthesis of NBD-Orn(Boc)-OBzl 0.998 g (5 mmol) of NBD-Cl was added in an eggplant-shaped flask by weight reduction, and dissolved with 100 mL of anhydrous methanol to obtain a yellow, clear, and transparent solution, and a stirring bar was added; 2.15 g (6 mmol) of HCl·Orn(Boc)-OBzl was added under ice-bath stirring, and an obtained mixed solution was adjusted to a pH value of 10 with 2.6 mL of DIPEA; the ice bath was removed, and reaction was conducted in the dark at a room temperature for 8 h, and it was observed that the color of a reaction solution gradually deepened to dark green, accompanied by green fluorescence; the reaction progress was monitored by TLC (according to a volume ratio, a developer was a mixture of PE:EA=2:1, $R_f$=0.30), and the reaction was determined to be complete after the disappearance of the NBD-Cl raw material was observed. After the reaction, an obtained system was separated and purified by a medium-pressure preparative column (a purification reagent was a mixture of EA and PE, where a volume fraction of the EA was 35%), to obtain 990 mg (41.2%) of a target product NBD-Orn(Boc)-OBzl as an orange-red solid powder, with bright green fluorescence in an organic solvent. ESI-MS (m/z): 484.5 $[M-H]^-$; 1H-NMR (300 MHz, DMSO-$d_6$): δ (ppm)=9.51 (s, 1H), 8.52 (d, J=8.9 Hz, 1H), 7.32 (s, 5H), 6.84 (s, 1H), 6.41 (s, 1H), 5.17 (s, 2H), 3.34 (s, 1H), 2.94 (q, J=6.1 Hz, 2H), 1.99 (m, 2H), 1.54 (m, 2H), 1.34 (s, 9H).

Synthesis of NBD-Orn(cycto) (ZD-D)

970 mg (2 mmol) of the NBD-Orn(Boc)-OBzl was added in an eggplant-shaped flask and dissolved with 5 mL of dry EA; in a fume hood, 10 mL of an HCl/EA solution (a concentration of HCl was 4 mol/L) was added dropwise to a resulting solution under stirring in an ice bath; a mouth of the flask was connected with a drying tube, and the solution was reacted for 3 h under stirring in an ice bath, and it was observed that an orange-red solid gradually precipitated along a wall of the flask; the progress of the reaction was monitored by TLC (according to a volume ratio, a developer was a mixture of EA:$H_2O$:acetic acid (HAc)=6:1:1, $R_f$=0.35), and the reaction was determined to be complete after the disappearance of the NBD-Orn(Boc)-OBzl raw material was observed. After the reaction was completed, under stirring in a warm water bath at 37° C., the eggplant-shaped flask was connected with a single pass having a plug, and the reaction solution was drained under reduced pressure with a vacuum circulating water pump, and a residue was reconstituted with 20 mL of the dry EA and then drained again; the above operations were repeated 3 times until there was no obvious acid gas residue, a residue was dissolved in 20 mL of methanol, an obtained mixed solution was adjusted to a pH value of 10 with triethylamine under stirring in an ice bath, and reacted in the dark for 6 h; the progress of the reaction was monitored by TLC (according to a volume ratio, a developer was a mixture of PE:EA=2:1, $R_f$=0.35), and the reaction was determined to be complete after the disappearance of the raw material was observed. After the reaction, an obtained system was separated and purified by a medium-pressure preparative column (a purification reagent was a mixture of EA and PE, where a volume fraction of the EA was 32%), to obtain 560 mg (76.3%) of a target product ZD-D as an orange-red solid powder. M.p.: 218.1-220.7° C.;

$$[\alpha]_D^{25} = -10.9,$$

(C=0.1, $CH_3OH$); ESI-MS (m/z): 300.3 $[M+Na]^+$; $^1H$-NMR (300 MHz, DMSO-$d_6$): δ (ppm)=9.35 (s, 1H), 8.52 (d, J=9.0 Hz, 1H), 7.86 (s, 1H), 6.54 (d, J=9.1 Hz, 1H), 4.64 (s, 1H), 3.21 (m, 2H), 2.16 (m, 2H), 1.90 (m, 2H).

Example 5

Synthesis of N-benzyloxycarbonyl-N-ε-tert-butoxycarbonyl-L-ornithylbenzylamine (Z-Orn(Boc)-NBzl)

3.660 g (10 mmol) of N-benzyloxycarbonyl-N-ε-tert-butoxycarbonyl-L-ornithine was added in an eggplant-shaped flask, and dissolved with 100 mL of anhydrous THF to obtain a colorless, clear, and transparent solution, and a stirring bar was added; under stirring in an ice bath, 1.620 g (12 mmol) of HOBt and 2.472 g (12 mmol) of DCC were added, activated for 10 min, and a white solid precipitated; 1.6 mL of benzylamine was added to the reaction system, and a resulting reaction solution was adjusted to a pH value of 8 with NMM; the ice bath was removed, and a reaction was conducted at a room temperature for 12 h; the reaction progress was monitored by TLC (according to a volume ratio, a developer was a mixture of dichloromethane:methanol=30:1), and the reaction was determined to be complete after the disappearance of the N-benzyloxycarbonyl-N-ε-tert-butoxycarbonyl-L-ornithine raw material was observed. After the reaction, a resulting product was filtered under reduced pressure, and the THF was spin-dried by rotary evaporation to obtain a yellow oily substance; 60 mL of ethyl acetate was added to the oily substance, and then sequentially subjected to extraction and washing with a saturated $NaHCO_3$ solution (25 mL×3), a saturated NaCl solution (25 mL×3), a 5 wt % $KHSO_4$ solution (25 mL×3), a saturated NaCl solution (25 mL×3), a 5 wt % $NaHCO_3$ solution (25 mL×3), and a saturated NaCl solution (25 mL×3); during the washing, the solution gradually became lighter to colorless, and after washing, anhydrous $Na_2SO_4$ was added to dry the solution for 2 h; the $Na_2SO_4$ was removed by normal-pressure filtration, and a filtrate was concentrated under reduced pressure to obtain a colorless oil; the colorless oil was separated and purified by a medium-pressure preparative column (according to a volume ratio, a purification reagent for collecting a product was a mixture of dichloromethane:methanol=95:5), to obtain 4.490 g (98.7%) of a target product Z-Orn(Boc)-NBzl, as a white solid. ESI-MS (m/e): 455 $[M+H]^+$; $^1H$-NMR (300 MHz, DMSO-$d_6$): δ (ppm)=8.39 (m, 1H), 7.42 (d, J=8.0 Hz, 1H), 7.34 (m, 5H), 7.27 (m, 5H), 6.79 (m, 1H), 5.03 (s, 2H), 4.28 (d, J=5.3 Hz, 2H), 3.99 (m, 1H), 2.89 (t, J=5.8 Hz, 2H), 1.60 (m, 2H), 1.51 (m, 2H), 1.37 (s, 9H).

Synthesis of N-ε-tert-butoxycarbonyl-L-ornithylbenzylamine (Orn(Boc)-NBzl)

4.490 g (9.9 mmol) of the Z-Orn(Boc)-NBzl was placed in an eggplant-shaped flask and dissolved in 40 mL of methanol to obtain a clear and transparent solution; 0.449 g of palladium on carbon (Pd/C) was added into the eggplant-shaped flask, a tee was installed, and stirring was started at the same time; a vertical side of the tee was connected to a hydrogen bag, a side port of the tee was connected to a water pump, and air in the eggplant-shaped flask was exhausted and replaced with hydrogen; after repeated air exchange three times, a reaction device was moved to a hydrogenolysis fume hood, and a reaction was conducted at a room temperature for 2 h; the reaction progress was monitored by TLC (according to a volume ratio, a developer was a mixture of dichloromethane:methanol=10:1), and the reaction was determined to be complete after the disappearance of the Z-Orn(Boc)-NBzl raw material was observed. After the reaction, a product was filtered under normal pressure to remove the palladium on carbon, and an obtained filtrate was spin-dried to obtain 3.988 g (88.8%) of a target product Orn(Boc)-NBzl as a white solid powder. ESI-MS (m/e): 321 $[M+H]^+$.

Synthesis of N-(7-nitro-2,1,3-benzoxadiazol-4-yl)-N-ε-tert-butoxycarbonyl-L-ornithylbenzylamine (NBD-Orn(Boc)-NBzl)

0.998 g (5 mmol) of 4-chloro-7-nitro-2,1,3-benzoxadiazole (NBD-Cl) and 1.942 g (6 mmol) of the Orn(Boc)-NBzl were added in an eggplant-shaped flask, and dissolved with 40 mL of anhydrous methanol to obtain a colorless, clear, and transparent solution, and a stirring bar was added; under stirring in an ice bath, the obtained system was adjusted to a pH value of to 10 with 2.6 mL of DIPEA; the ice bath was removed, and reaction was conducted at a room temperature for 5 h; the reaction progress was monitored by TLC (according to a volume ratio, a developer was a mixture of petroleum ether:ethyl acetate=2:1), and the reaction was determined to be complete after the disappearance of the NBD-Cl raw material was observed. After the reaction, an obtained system was spin-dried under reduced pressure, and an obtained residue was separated and purified by a medium-pressure preparative column (a purification reagent was a mixture of EA and PE, where a volume fraction of the EA was 35%), to obtain 2.028 g (83.8%) of a target product NBD-Orn(Boc)-NBzl as an orange-red solid powder, with bright green fluorescence in an organic solvent. ESI-MS (m/e): 483.4 $[M-H]^-$.

Synthesis of (S)-5-amino-N-benzyl-2-((7-nitro-2,1,3-benzoxadiazol-4-yl)amino)pentaneamide (NBD-Orn(HCl)-NBzl, ZD-E)

2.028 g (5.5 mmol) of the NBD-Orn(Boc)-NBzl was placed in an eggplant-shaped flask, dissolved with 10 mL of dry ethyl acetate to obtain a colorless, clear, and transparent solution, and a stirring bar was added; under stirring in an ice bath, 20 mL of a HCl/EA solution (a concentration of HCl was 2 mol/L) was added in a fume hood, and a mouth of the flask was connected with a drying tube; a reaction was conducted by stirring in an ice bath for 2 h; the reaction progress was monitored by TLC (according to a volume ratio, a developer was a mixture of ethyl acetate:water:glacial acetic acid=6:1:1), and the reaction was determined to be complete after the disappearance of the NBD-Orn(Boc)-NBzl raw material was observed. After the reaction was completed, the solvent was removed by suction filtration, an obtained residue was added with 15 mL of dry ethyl acetate×3 times, 15 mL of diethyl ether×1 time, and the solvent was removed by suction filtration to obtain 1.762 g (96.1%) of a target product (in a hydrochloride form), namely the (S)-5-amino-N-benzyl-2-((7-nitro-2,1,3-benzoxadiazol-4-yl)amino)pentaneamide hydrochloride, as a red solid. ESI-MS (m/e): 384 $[M+H]^+$.

Example 6

Synthesis of (S)—N-benzyl-5-(2-chloroacetimido)-2-((7-nitro-2,1,3-benzoxadiazol-4-yl)amino)pentaneamide (NBD-Orn(Cl)-NBzl, ZD-E-1)

420 mg (1 mmol) of the (S)-5-amino-N-benzyl-2-((7-nitro-2,1,3-benzoxadiazol-4-yl)amino)pentaneamide hydrochloride was added in an eggplant-shaped flask, and dissolved with 40 mL of anhydrous methanol to obtain a colorless, clear, and transparent solution, and a stirring bar was added; under stirring in an ice bath, 187 mg (1.2 mmol) of ethyl 2-chloroacetimidate hydrochloride was added, and a resulting system was adjusted to a pH value of 10 with DIPEA; the ice bath was removed, and reaction was conducted at a room temperature for 6 h; the reaction progress was monitored by TLC (according to a volume ratio, a developer was a mixture of ethyl acetate:water:glacial acetic acid=6:1:1), and the reaction was determined to be complete after the disappearance of the (S)-5-amino-N-benzyl-2-((7-nitro-2,1,3-benzoxadiazol-4-yl)amino)pentaneamide hydrochloride raw material was observed. After the reaction was completed, the solvent was removed by spin-drying, an obtained residue was re-dissolved with a 5% methanol aqueous solution, separated and purified by C18 silica gel column chromatography (a reagent was a 60% methanol aqueous solution by volume fraction); a purified product was spinned to remove the methanol, lyophilized to remove water, to obtain 210 mg (50.0%) of a target product ZD-E-1, as an orange-red solid powder. The purity was: 97.34%; M.p.: 88.2-90.0° C.;

$$[\alpha]_D^{25} = -14.0,$$

(C=0.1, $CH_3OH$); ESI-MS (m/z): 458.7 $[M-H]^-$; 1H-NMR (300 MHz, DMSO-$d_6$): δ (ppm)=9.94 (s, 1H), 9.52 (s, 1H), 9.35 (s, 1H), 9.09 (s, 1H), 8.79 (s, 1H), 8.56 (d, J=8.7 Hz, 1H), 7.26 (m, 5H), 6.36 (s, 1H), 4.40 (m, 1H), 4.36 (s, 2H), 4.31 (m, 2H), 3.29 (m, 2H), 2.03 (m, 2H), 1.68 (m, 2H); 13C-NMR (75 MHz, DMSO-$d_6$): δ/ppm=170.2, 167.3, 162.8, 158.9, 158.4, 139.4, 128.7, 127.7, 127.3, 118.2, 114.4, 58.6, 42.8, 42.2, 41.4, 24.7, 24.3.

Example 7

Synthesis of Z-Lys(Boc)-NBzl 3.8 g (10 mmol) of Z-Lys(Boc)-OH was added into an eggplant-shaped flask by weight reduction, and dissolved with 100 mL of anhydrous THF to obtain a colorless, clear, and transparent solution, and a stirring bar was added; under stirring in an ice bath, 1.62 g (12 mmol) of HOBt and 2.47 g (12 mmol) of DCC were sequentially added, and after activation for 10 min, there was white solid precipitated; 5.6 mL of benzylamine was added dropwise to the eggplant-shaped flask, and a mixed solution was adjusted to a pH value of 8 with NMM; the ice bath was removed, and a reaction was conducted for 8 h by stirring at a room temperature; the progress of the reaction was monitored by TLC (according to a volume ratio, a developer was a mixture of $CH_2Cl_2$:$CH_3OH$=30:1, $R_f$=0.38), and the reaction was determined to be complete after the disappearance of the Z-Lys(Boc)-OH raw material was observed. After the reaction, a product was filtered under reduced pressure with a vacuum circulating water pump, a filter cake was rinsed with EA, and a filtrate was concentrated to dryness under reduced pressure to remove THF; a residue was dissolved with 150 mL of EA, the solid material was removed by suction filtration, and a resulting filtrate was transferred to a 250 mL separatory funnel; the filtrate was sequentially subjected to extraction and washing with a saturated $NaHCO_3$ solution 3 times (30 mL/time), a saturated NaCl solution 3 times (30 mL/time), a 5 wt % $KHSO_4$ solution 3 times (30 mL/time), a saturated NaCl solution 3 times (30 mL/time), a saturated $NaHCO_3$ solution 3 times (30 mL/time), and a saturated NaCl solution 3 times (30 mL/time), and it was observed that the color of the EA layer became light to colorless during the extraction and washing; after the EA layer was dried with anhydrous $Na_2SO_4$ for 2 h, the $Na_2SO_4$ was removed by filtration, and a filtrate was concentrated under reduced pressure to obtain a colorless oil; the colorless oil was separated and purified by a medium-pressure preparative column (a purification reagent was a mixture of methanol and dichloromethane, and a volume fraction of the methanol was 5%) to obtain 3.85 g (82.3%) of a target product Z-Lys(Boc)-NBzl, as a white solid powder. ESI-MS (m/z): 469 $[M+H]^+$.

Synthesis of Lys(Boc)-NBzl 2.34 g (5 mmol) of the Z-Lys(Boc)-NBzl was placed in an eggplant-shaped flask and dissolved in 50 mL of methanol to obtain a colorless, clear, and transparent solution; under stirring, 234 mg of Pd/C was added in the eggplant-shaped flask; the eggplant-shaped flask was connected with a tee and a hydrogen bag, and air in the flask was pumped out with a vacuum circulating water pump, and hydrogen gas was introduced; the above operations were repeated 3 times, the eggplant-shaped flask was kept in communication with the hydrogen bag, and a reaction was conducted by stirring at a room temperature in a fume hood for 3 h; the progress of the reaction was monitored by TLC (according to a volume ratio, a developer was a mixture of $CH_2Cl_2$:$CH_3OH$=10:1, $R_f$=0.25), and the reaction was determined to be complete after the disappearance of the Z-Lys(Boc)-NBzl raw material was observed. After the reaction, a product was filtered under normal pressure to remove the Pd/C, and an obtained filtrate was spin-dried to obtain 1.59 g (95.2%) of a target product Lys(Boc)-NBzl as a white solid powder. ESI-MS (m/z): 335 $[M+H]^+$.

Synthesis of NBD-Lys(Boc)-NBzl 0.998 g (5 mmol) of 4-chloro-7-nitro-2,1,3-benzoxadiazole (NBD-Cl) was added in an eggplant-shaped flask by weight reduction, and dissolved with 100 mL of anhydrous methanol to obtain a yellow, clear, and transparent solution, and a stirring bar was added; 2.0 g (6 mmol) of the Lys(Boc)-NBzl was added under ice-bath stirring, and an obtained mixed solution was adjusted to a pH value of 10 with 2.6 mL of DIPEA; the ice bath was removed, and reaction was conducted in the dark at a room temperature for 8 h, and it was observed that the color of a reaction solution gradually deepened to dark green, accompanied by green fluorescence; the reaction progress was monitored by TLC (according to a volume ratio, a developer was a mixture of PE:EA=2:1, $R_f$=0.30), and the reaction was determined to be complete after the disappearance of the NBD-Cl raw material was observed. After the reaction, an obtained system was separated and purified by a medium-pressure preparative column (a purification reagent was a mixture of EA and PE, where a volume fraction of the EA was 35%), to obtain 900 g (36.2%) of a target product NBD-Lys(Boc)-NBzl as an orange-red solid powder, with bright green fluorescence in an organic solvent. ESI-MS (m/z): 497.5 $[M-H]^-$; 1H-NMR (300 MHz, DMSO-$d_6$): δ (ppm)=9.36 (s, 1H), 8.73 (s, 1H), 8.53 (d, J=8.8 Hz, 1H), 7.28 (m, 5H), 6.77 (t, J=5.1 Hz, 1H), 6.34 (s, 1H), 4.36 (m, 1H), 4.30 (s, 2H), 2.89 (s, 2H), 1.95 (s, 2H), 1.40 (m, 4H), 1.33 (m, 9H).

Synthesis of NBD-Lys(HCl)-NBzl (ZD-F)

1.49 g (3 mmol) of the NBD-Lys(Boc)-NBzl was added in an eggplant-shaped flask and dissolved with 5 mL of dry ethyl acetate; in a fume hood, 15 mL of an HCl/EA solution (a concentration of HCl was 4 mol/L) was added dropwise to a resulting solution under stirring in an ice bath; a mouth of the flask was connected with a drying tube, and the solution was reacted for 3 h under stirring in an ice bath, and it was observed that an orange-red solid gradually precipitated along a wall of the flask; the progress of the reaction was monitored by TLC (according to a volume ratio, a developer was a mixture of EA:$H_2O$:HAc=6:1:1, $R_f$=0.35), and the reaction was determined to be complete after the disappearance of the NBD-Lys(Boc)-NBzl raw material was observed. After the reaction was completed, under stirring in a warm water bath at 37° C., the eggplant-shaped flask was connected with a single pass having a plug, and the reaction solution was drained under reduced pressure with a vacuum circulating water pump, and a residue was reconstituted with 20 mL of the dry EA and then drained again; the above operations were repeated 3 times until there was no obvious acid gas residue, and anhydrous diethyl ether was added for grinding, washing, and drying to obtain 1.24 g (95.4%) of a target product ZD-F (specifically in the form of a hydrochloride), as an orange-red solid powder.

Example 8

Synthesis of NBD-Lys(C1)-NBzl (ZD-F-1)

1.3 g (3 mmol) of NBD-Lys(HCl)-NBzl was added in an eggplant-shaped flask, and dissolved with 50 mL of anhydrous methanol to obtain an orange-red, clear, and transparent solution, and a stirring bar was added; 0.499 g (3.2 mmol) of ethyl 2-chloroacetimidate hydrochloride was added under ice-bath stirring, and an obtained mixed solution was adjusted to a pH value of 10 with 3.6 mL of DIPEA; the ice bath was removed, and reaction was conducted in the dark at a room temperature for 8 h; the reaction progress was monitored by TLC (according to a volume ratio, a developer was a mixture of EA:$H_2O$:HAc=6:1:1, $R_f$=0.38), and developed with ninhydrin, and the reaction was determined to be complete after the disappearance of the NBD-Lys(HCl)-NBzl raw material was observed. After the reaction was completed, the solvent was removed by spin-drying, an obtained residue was re-dissolved with a 5% methanol aqueous solution, separated and purified by C18 silica gel column chromatography (a reagent was a 40% methanol aqueous solution by volume fraction); a purified product was concentrated under reduced pressure to remove methanol, and lyophilized to remove water by a vacuum freeze dryer, to obtain 520 g (36.9%) of a target product ZD-F-1, as an orange-red solid powder. M.p.: 118.1-120.4° C.;

$$[\alpha]_D^{25} = -17.1,$$

(C=0.1, $CH_3OH$); ESI-MS (m/z): 472.4 $[M-H]^-$; 1H-NMR (300 MHz, DMSO-$d_6$): δ (ppm)=10.26 (s, 1H), 9.61 (s, 1H), 9.22 (s, 1H), 8.96 (t, J=5.3 Hz, 1H), 8.52 (d, J=8.8 Hz, 1H), 7.26 (m, 5H), 6.41 (s, 1H), 4.47 (m, 1H), 4.43 (s, 2H), 4.31 (d, J=5.1 Hz, 2H), 3.27 (t, J=5.9 Hz, 2H), 2.00 (m, 2H), 1.60 (m, 2H), 1.47 (m, 2H); 13C-NMR (75 MHz, DMSO-$d_6$): δ/ppm=170.5, 162.6 139.5, 128.7, 127.7, 127.3, 49.0, 42.8, 42.4, 39.6, 27.0, 23.6.

Test Example 1 Nanomorphology Characterization and Stability Research

Figure 1B:
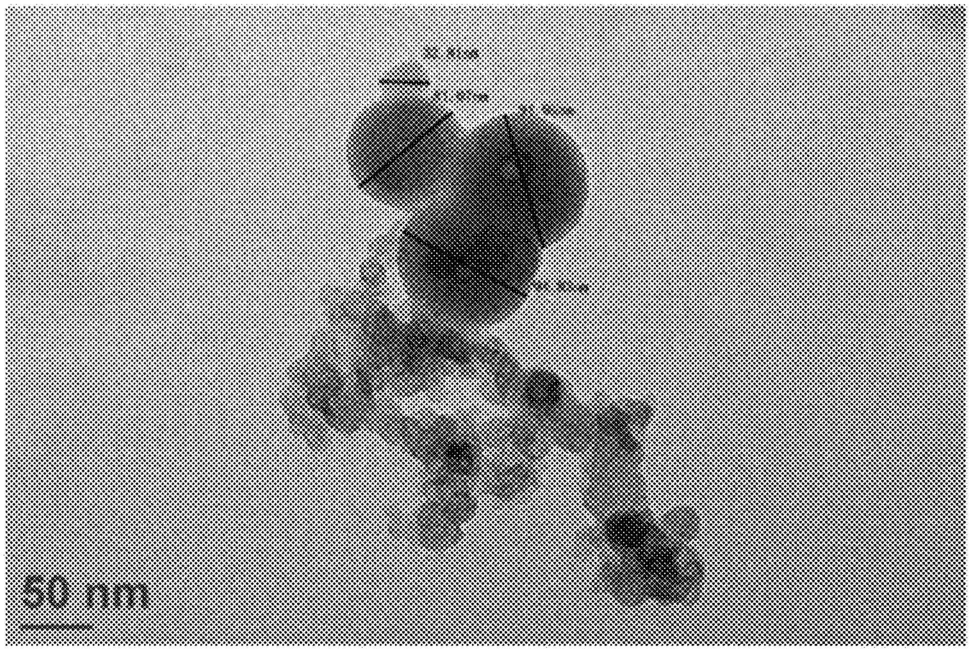
Figure 1C:
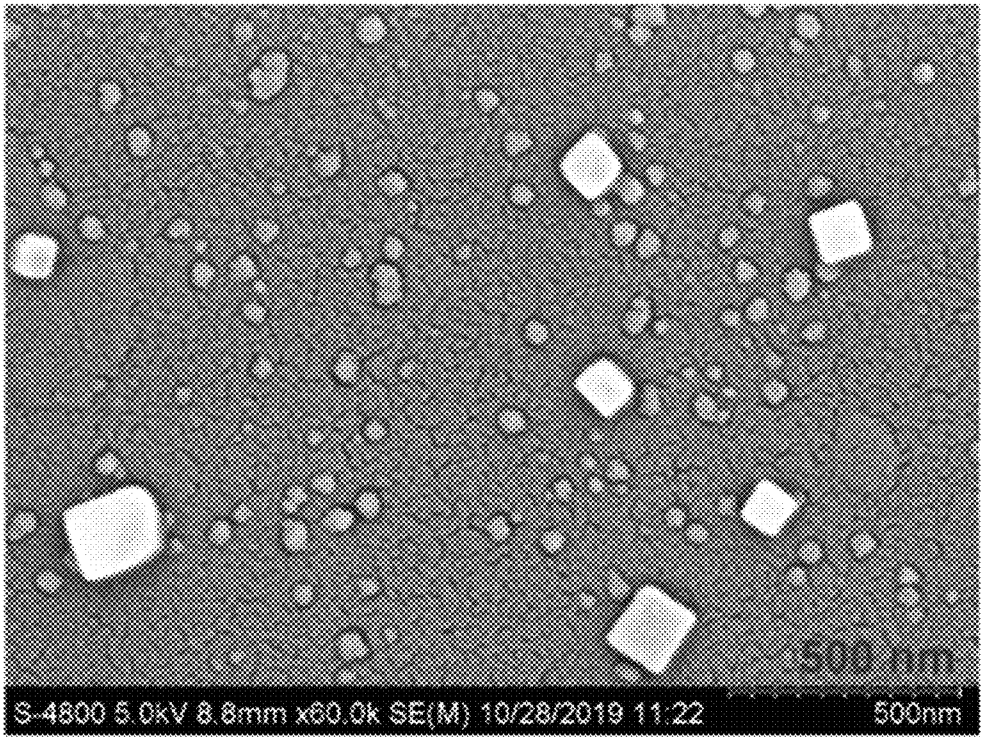
Figure 1D:
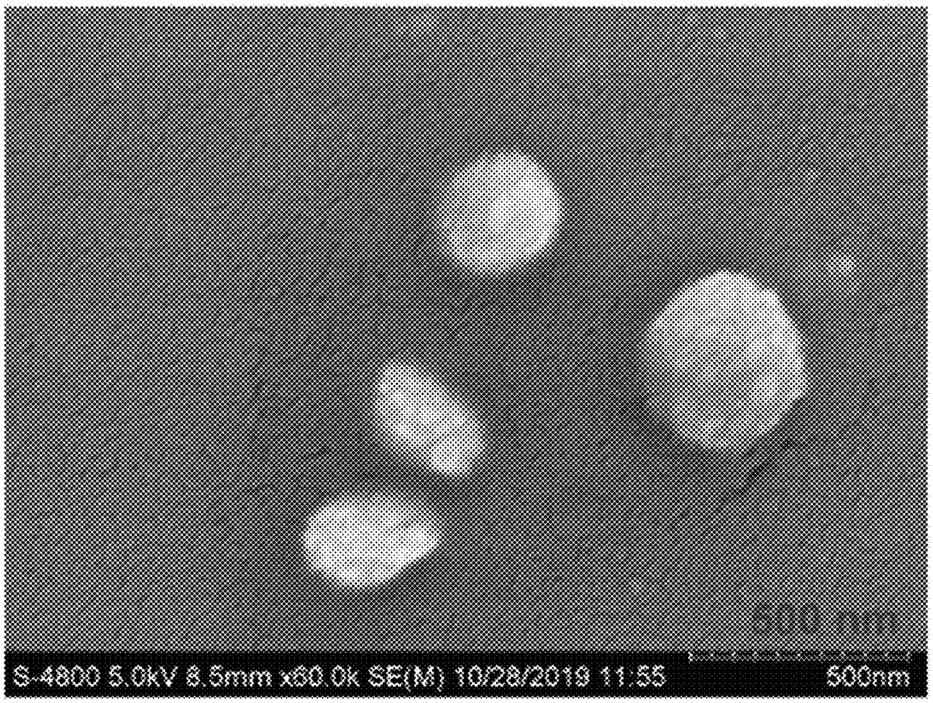
Figure 1E:
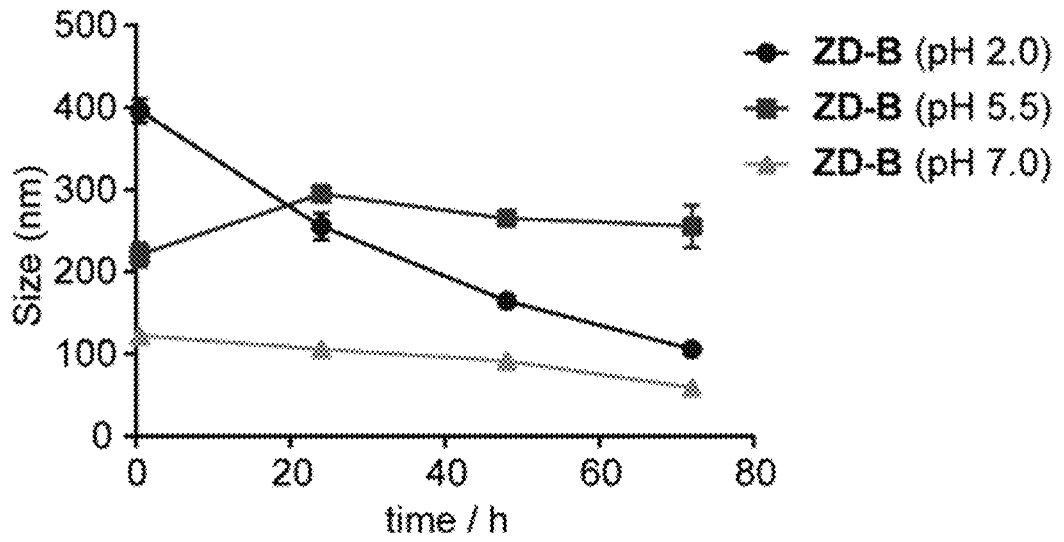
Figure 1F:
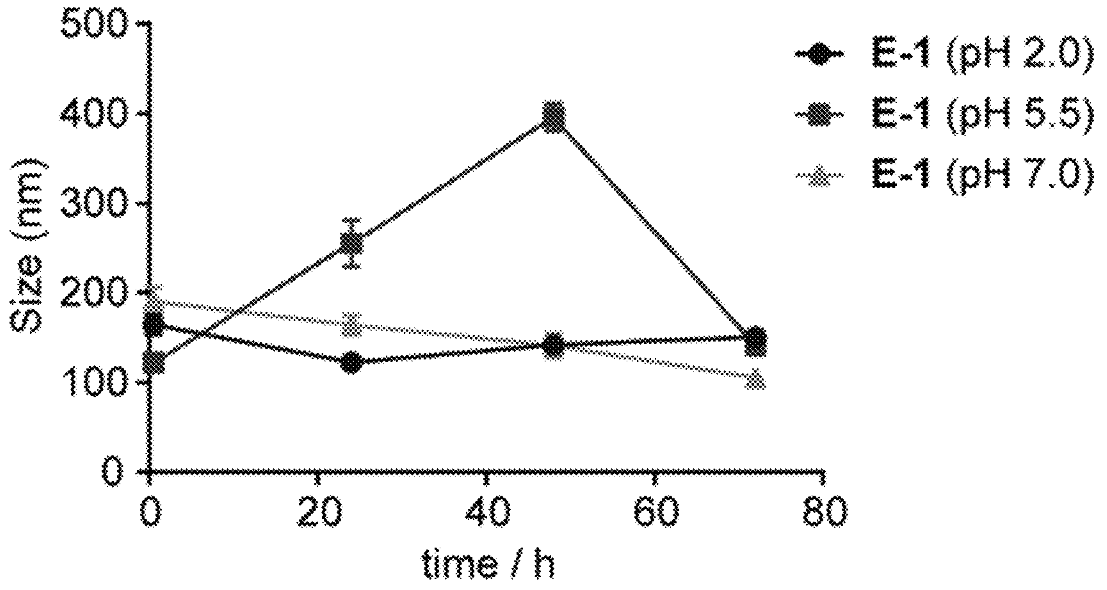
Figure 1G:
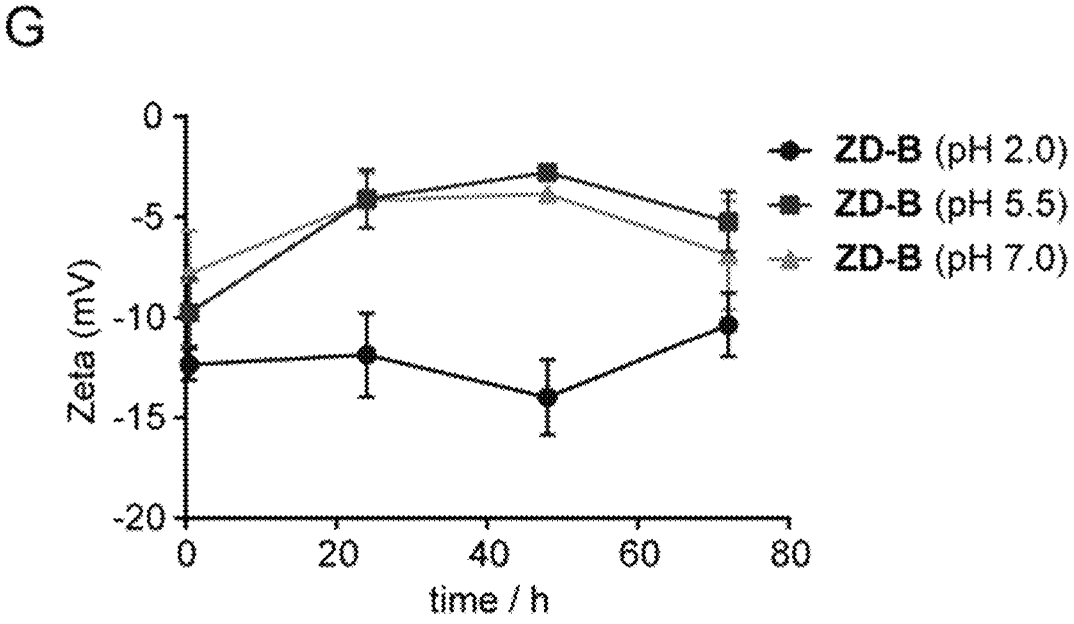
Figure 1H:
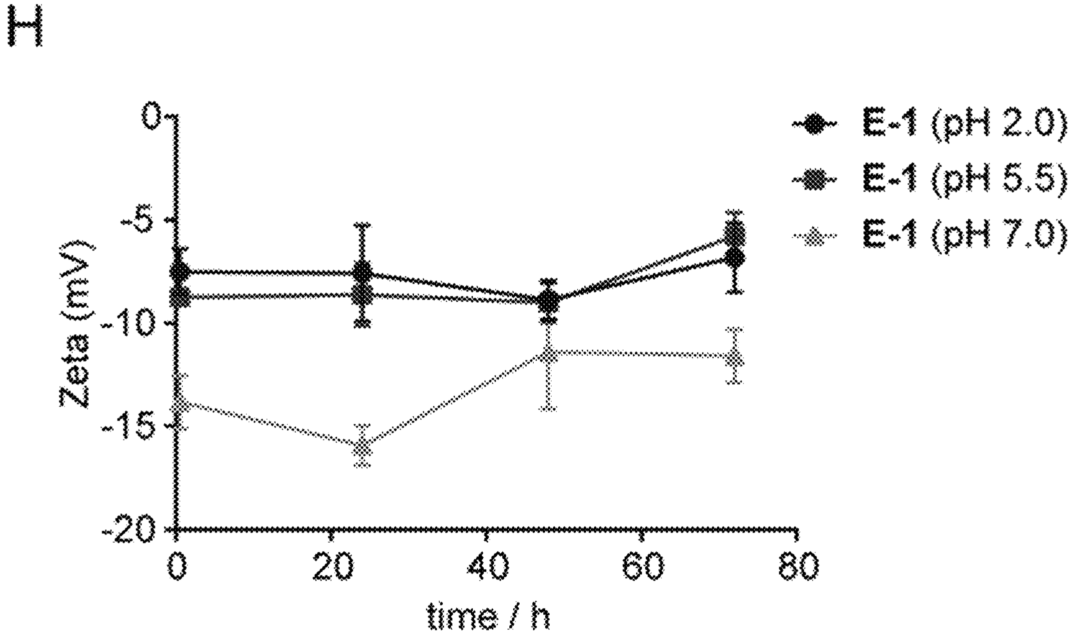

The nanomorphology of compounds ZD-B and ZD-E-1 were studied by TEM and SEM, and hydration particle size and Zeta potential of the two compounds in a solution were studied by a nanometer particle size analyzer. The results were shown in FIG. 1A-H. In FIG. 1A-H, FIG. 1A was a TEM image of the compound ZD-B; FIG. 1B was a TEM image of the compound ZD-E-1; FIG. 1C was a SEM image of the compound ZD-B; FIG. 1D was a SEM image of the compound ZD-E-1; FIG. 1E was a hydration particle size change curve of the compound ZD-B in solutions at different pH values within 72 h (0.5 h, 24 h, 48 h, and 72 h); FIG. 1F was a hydration particle size change curve of the compound ZD-E-1 in solutions at different pH solutions within 72 h; FIG. 1G was a Zeta potential change curve of the compound ZD-B in solutions at different pH values within 72 h; and FIG. 1H was a Zeta potential change curve of the compound ZD-E-1 in solutions at different pH values within 72 h. As shown in FIG. 1A-H, the ZD-B was in the shape of a strip, and the ZD-E-1 was in the shape of a ball. In the particle size change curve measured continuously for 72 h by the nanometer particle size analyzer: the ZD-B and ZD-E-1 each were at the smallest particle size at pH=7.0; the ZD-B had a great change in particle size at pH=2.0 and 5.5; and the ZD-E-1 had a particle size hardly changed at pH=2.0, and a particle size increased and then decreased at pH=5.5. In the Zeta potential change curve measured continuously for 72 h, neither ZD-B nor ZD-E-1 had an obvious change.

Test Example 2 Evaluation of In Vitro Anti-Tumor Cell Proliferation Activity of Fluorescently-Traceable Amino Acid Derivatives (by MTT Method)

Tested cell lines S180 (mouse ascites tumor cells), LLC (mouse lung cancer cells), A549 (human non-small cell lung cancer cells), HCT116 (human colon cancer cells), U2Os (human osteosarcoma cells), and MCF-7 (human breast cancer cells) each were purchased from Nanjing KeyGen Biotech. Inc.

When preparing a test sample, the test compound was prepared into a sample solution with a concentration of 500 μM (with a final concentration 100 μM) by a PBS buffer containing 0.5% DMSO, which was used for preliminary screening of an anti-cell proliferation experiment in vitro. For the compounds whose half inhibitory concentration ($IC_{50}$ value) to the tested cell line was lower than 100 μM, the sample solution was serially diluted to 50 μM, 25 μM, 12.5 μM, 6.25 μM, and 3.125 μM, the $IC_{50}$ value of the compounds to the tested cell line was detected by the MTT method again, and the measurement was repeated at least three times under the same experimental conditions until an obtained $IC_{50}$ value was stable and reliable.

Positive control group: doxorubicin, prepared to a required concentration with PBS buffer containing 0.5% DMSO; negative control group: a PBS buffer containing 0.5% DMSO; blank group: a PBS buffer containing 0.01% DMSO.

A specific process was as follows:

1) Cell inoculation: cells in well growth condition and in a logarithmic growth phase were diluted with a medium to a cell concentration of $3\times10^4$ cells/mL to $5\times10^4$ cells/mL, and inoculated evenly in a 96-well plate, at 100 μL per well (peripheral wells were sealed with 100 μL of the PBS buffer); the cell-inoculated 96-well plate was incubated in a cell culture incubator at 37° C. and 5% $CO_2$ for 8 h.

2) Administration: cell growth and adhesion were observed; when a cell adhesion rate reached over 50%, 25 μL of different compounds or test sample solutions of different concentrations were administrated according to preset multiple wells, and negative and positive control groups and a Blank group were set up for each plate; the plate was gently tapped to disperse the sample solution evenly, and then incubated in a cell culture incubator for 48 h.

3) Post-treatment: 25 μL of a pre-prepared MTT solution was added to each well, continued to incubate for 4 h, and then taken out; after discarding a supernatant (suspended cells needed to be centrifuged at 3,000 rpm for 10 min), 150 μL of DMSO was added to each well and shaken on a cell shaker for 15 min to fully dissolve formazan; with a microplate reader, an OD value of each well was measured at a wavelength of 570 nm (an ideal range was 0.3 to 1.4).

An inhibition rate of the anti-cell proliferation activity of the test compound was calculated according to formula a, each experiment was repeated at least three times, and the $IC_{50}$ value of the test compound was calculated in prism, and the results were shown in Table 1.

$$\text{Inhibition rate} = [\text{average } OD \text{ value of negative control group} - \text{average } OD \text{ value of test compound group}) / \text{average } OD \text{ value of negative control group} - \text{average } OD \text{ value of Blank group}] \times 100\%. \quad \text{formula a}$$

TABLE 1

$IC_{50}$ values of in vitro anti-cell proliferation activity of test compounds to cell lines (Mean ± SD μM)

| Test compound | S180 | LLC | A549 | HCT116 | U2Os | MCF-7 |
|---|---|---|---|---|---|---|
| DOX | 0.490 ± 0.092 | 0.190 ± 0.095 | 0.229 ± 0.052 | 0.375 ± 0.108 | 1.201 ± 0.034 | 1.032 ± 0.188 |
| ZD-A | >100 | >100 | >100 | >100 | >100 | >100 |
| ZD-B | 74.360 ± 10.100 | 96.483 ± 6.846 | >100 | >100 | 86.427 ± 5.299 | 105.719 ± 1.333 |
| ZD-C | >100 | >100 | >100 | >100 | >100 | >100 |
| ZD-D | >100 | >100 | >100 | >100 | >100 | >100 |
| ZD-E | 65.963 ± 2.612 | >100 | >100 | 49.703 ± 4.166 | 60.539 ± 0.969 | 85.240 ± 6.096 |
| ZD-E-1 | 24.641 ± 1.716 | 26.112 ± 2.582 | 45.548 ± 0.672 | 22.569 ± 1.450 | 28.801 ± 1.143 | 40.484 ± 1.908 |
| ZD-F | >100 | >100 | >100 | >100 | >100 | >100 |
| ZD-F-1 | 23.710 ± 2.295 | >100 | >100 | 38.890 ± 2.047 | 45.724 ± 1.680 | 68.723 ± 1.502 |

Test Example 3 Evaluation of Fluorescently-Traceable Amino Acid Derivatives Inhibiting Tumor Growth In Vivo (Mouse 5180 Fibrosarcoma Model)

The mice used in the experiment were male ICR mice of SPF grade, weighing 20 g±2 g, purchased from Beijing Vital River Laboratory Animal Technology Co., Ltd., and raised in an animal barrier of the Experimental Animal Department of Capital Medical University.

The specific method included: drugs were administered to tumor-forming mice by group for 7 consecutive days, a length of the tumor was measured every other day to calculate a tumor volume. 24 h after the last administration, the mice were weighed, anesthetized with diethyl ether, and eyeballs were removed to collect blood; the obtained whole blood was centrifuged at 1,000 rpm for 10 min, and a serum was absorbed for later use. The mice were sacrificed by neck dislocation, and the tumor mass and various organs were stripped and weighed (it was ensured that the operation was done as soon as possible and the stripping was complete and clean). The tumor inhibition rate was calculated by formula b, the results were shown in Table 2 and FIG. 2; and by calculating a viscera-weight ratio of each organ, and it was analyzed whether the test compound had obvious physiological effects on the mouse organs.

$$\text{Tumor inhibition rate} = (\text{average tumor weight in Vehicle group} - \text{average tumor weight in treatment group}) / \text{avaerage tumor weight in Vehicle group} \times 100\%. \quad \text{formula b}$$

1) Comparison Between Different Test Compounds

TABLE 2

In vivo administration grouping and result statistics of test compounds

| Group | Administration dosage (μmol/kg) | Average tumor weight (Mean ± SD g) | Tumor inhibition rate |
|---|---|---|---|
| Vehicle | / | 1.787 ± 0.462 | / |
| DOX | 2 | 0.861 ± 0.462** | 51.80% |
| YW3-56 | 10 | 0.994 ± 0.310** | 44.39% |

TABLE 2-continued

| In vivo administration grouping and result statistics of test compounds | | | |
|---|---|---|---|
| Group | Administration dosage (μmol/kg) | Average tumor weight (Mean ± SD g) | Tumor inhibition rate |
| ZD-A | 10 | 1.140 ± 0.437* | 36.19% |
| ZD-B | 10 | 0.990 ± 0.180** | 44.60% |
| ZD-C | 10 | 1.260 ± 0.466* | 29.46% |
| ZD-D | 10 | 1.326 ± 0.318 | 25.77% |
| ZD-E | 10 | 1.326 ± 0.685 | 25.82% |
| ZD-E-1 | 10 | 1.072 ± 0.386** | 40.01% |

Figure 2:
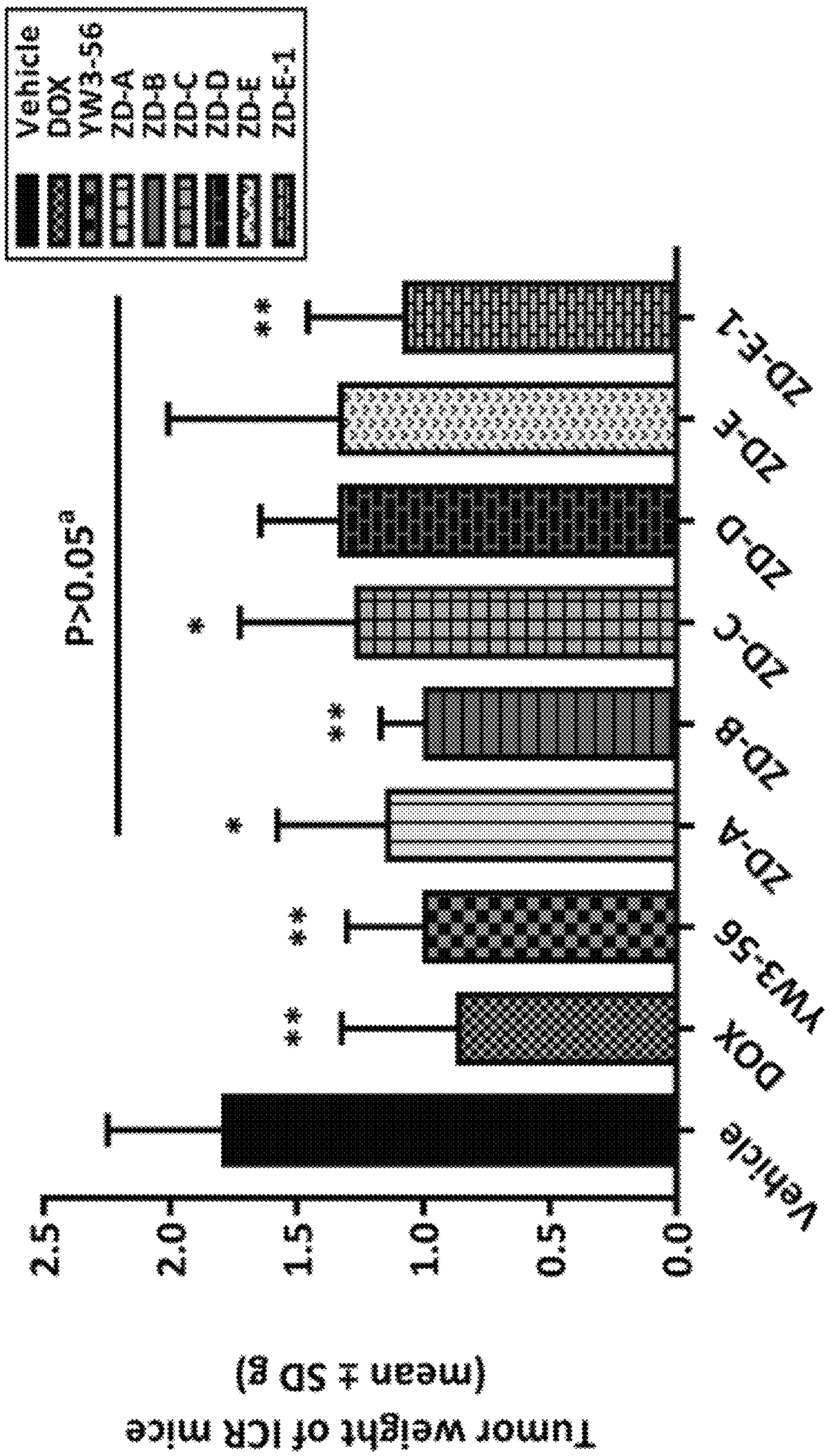
FIG. 2 shows antitumor activities of different test compounds in a mouse S180 sarcoma model.

Note:

"YW3-56" in Table 2 had a chemical name of N-(1-(benzylamino)-5-(2-chlorooxalimide)-1-oxopentan-2-yl)-6-(dimethylamino)-2-naphthylamide, which was prepared by a method disclosed in Patent US20120108562 (Gong Chen, Yanming Wang, Pingxin Li, Jing Hu, Shu Wang, Yuji Wang. Therapeutic compositions and methods);

ip indicated intraperitoneal injection; n was 10;

After one-way analysis of variance, *meant that compared with the Vehicle group, there was a difference, $P < 0.05$; **represented a significant difference compared with the Vehicle group, $P < 0.01$; and a represented no difference compared with the YW3-56 group, $P > 0.05$ (FIG. 2).

In the above experiments, the same dosage was selected, and intraperitoneal injection was adopted; and a lead compound YW3-56 and main compounds containing different amino acids were initially evaluated using doxorubicin as a positive control group. Through one-way analysis of variance, it was found that the average tumor weight of compounds ZD-A and ZD-C was different from that of Vehicle group, while the average tumor weight of ZD-B and ZD-E-1 was significantly different from that of Vehicle group; moreover, there was no difference in the average tumor weight of all the tested compounds compared with the YW3-56 group. The results in Table 2 and FIG. 2 showed that these tested compounds all exhibited certain anti-tumor growth activities at a dosage of 10 μmol/kg, among which ZD-B and ZD-E-1 had the most prominent activities.

2) Dose-Effect Analysis of Dominant Compounds

Based on the above results, several compound structures with in vivo anti-tumor growth activity and modifiable sites were obtained, and further dose-effect analysis was conducted. The results were shown in Table 3 and FIG. 3.

TABLE 3

| In vivo administration grouping and result statistics of main compounds for dominant amino acids | | | | |
|---|---|---|---|---|
| Group | Administration dosage (μmol/kg) | Administration route | Average tumor weight (Mean ± SD g) | Tumor Inhibition Rate |
| Vehicle | / | iv | 1.715 ± 0.279 | / |
| YW3-56 | 10 | iv | 0.954 ± 0.298** | 44.38% |
| ZD-E-1 | 10 | iv | 0.982 ± 0.300** | 42.73% |
| | 5 | iv | 1.001 ± 0.196** | 41.65% |
| | 2 | iv | 1.042 ± 0.205** | 39.23% |
| ZD-F-1 | 10 | iv | 1.029 ± 0.423** | 39.99% |
| | 5 | iv | 1.191 ± 0.407** | 30.54% |
| | 2 | iv | 1.487 ± 0.660* | 13.32% |
| ZD-A | 10 | ip | 1.204 ± 0.438* | 29.78% |
| | 5 | ip | 1.232 ± 0.102** | 28.20% |
| | 2 | ip | 1.315 ± 0.338* | 23.36% |
| ZD-B | 10 | ip | 1.008 ± 0.472** | 41.23% |
| | 5 | ip | 1.104 ± 0.218** | 35.64% |
| | 2 | ip | 1.424 ± 0.434* | 17.00% |

Note:

ip meant intraperitoneal injection; iv meant tail intravenous injection; n was 10.

Figure 3:
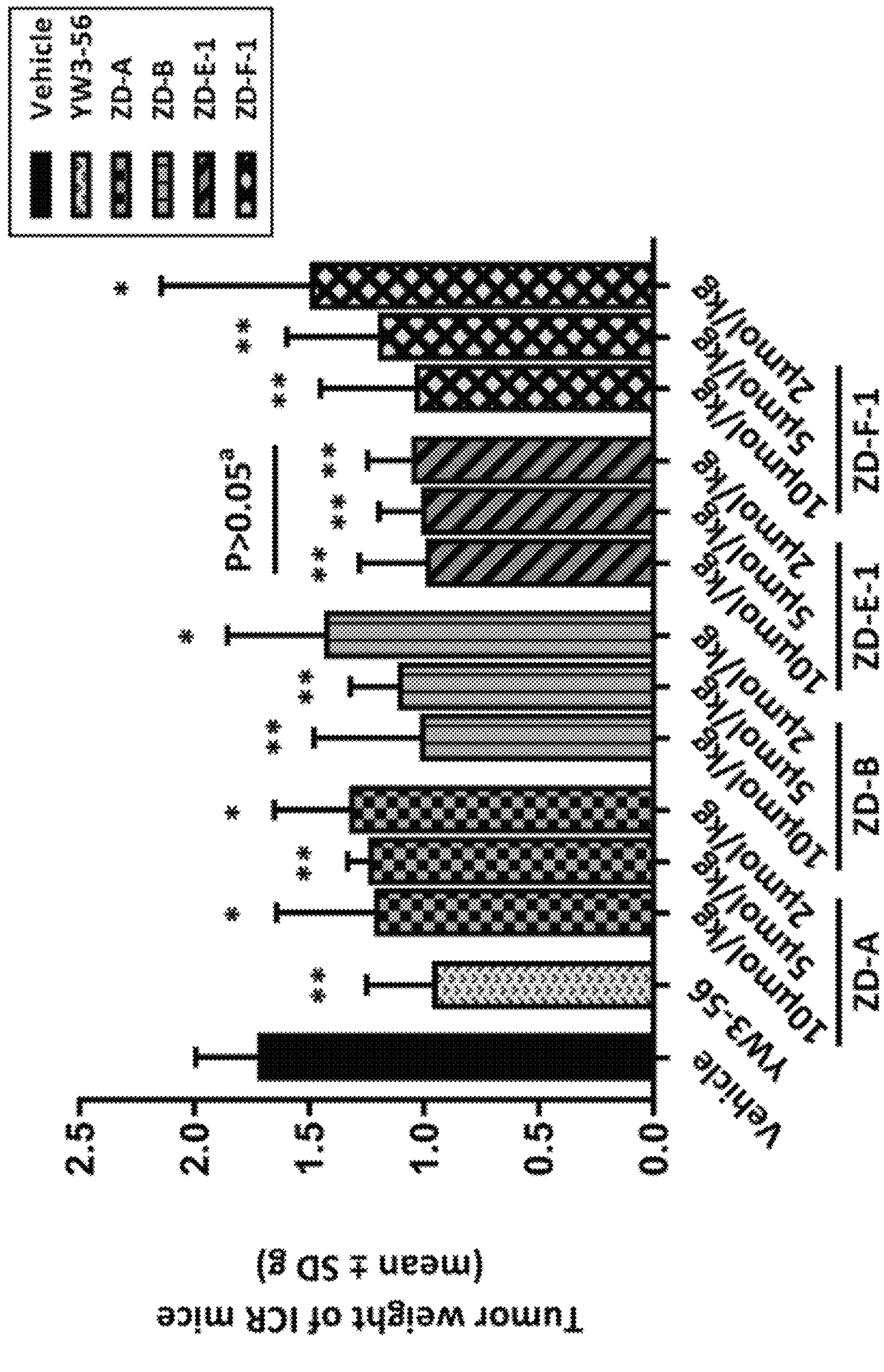
FIG. 3 shows antitumor activities of dominant test compounds in the mouse S180 sarcoma model.

After one-way analysis of variance, *meant that compared with the Vehicle group, there was a difference, $P < 0.05$; **represented a significant difference compared with the Vehicle group, $P < 0.01$; and a represented no difference compared with the YW3-56 group, $P > 0.05$ (FIG. 3).

After a preliminary study on the in vivo anti-tumor growth activity of different amino acid main compounds, ZD-A, ZD-B, ZD-E-1, and ZD-E-1 with an increased side-chain methylene unit (ZD-F-1) were selected; three dosages of 10 μmol/kg, 5 μmol/kg, and 2 μmol/kg were set to evaluate the inhibitory ability of the four compounds on tumor growth in mice. Due to poor water solubility, ZD-A and ZD-B could only adopt intraperitoneal injection; however, ZD-E-1 and ZD-F-1 had no such concerns, and could adopt tail intravenous injection. After one-way analysis of variance, it was found that at the dosage of 2 μmol/kg, the average tumor weight of these four compounds was still different from that of the Vehicle group. The ZD-E-1 showed the most significant activity, which had significant differences compared with the Vehicle group under the three dosages, and had no difference compared with the YW3-56 group. The experimental results showed that the compound ZD-E-1 exhibited a desirable and stable anti-tumor growth activity at three dosages, which was superior to its analogue ZD-F-1. Afterwards, the tumor growth trend and the viscera-weight ratio of the two compounds on mice were analyzed to compare the anti-tumor growth ability and toxicity of the two compounds. The results were shown in FIG. 4 and FIG. 5: after one-way analysis of variance, * meant that compared with the Vehicle group, there was a difference, $P<0.05$; ** represented a significant difference compared with the Vehicle group, $P<0.01$.

Figure 5:
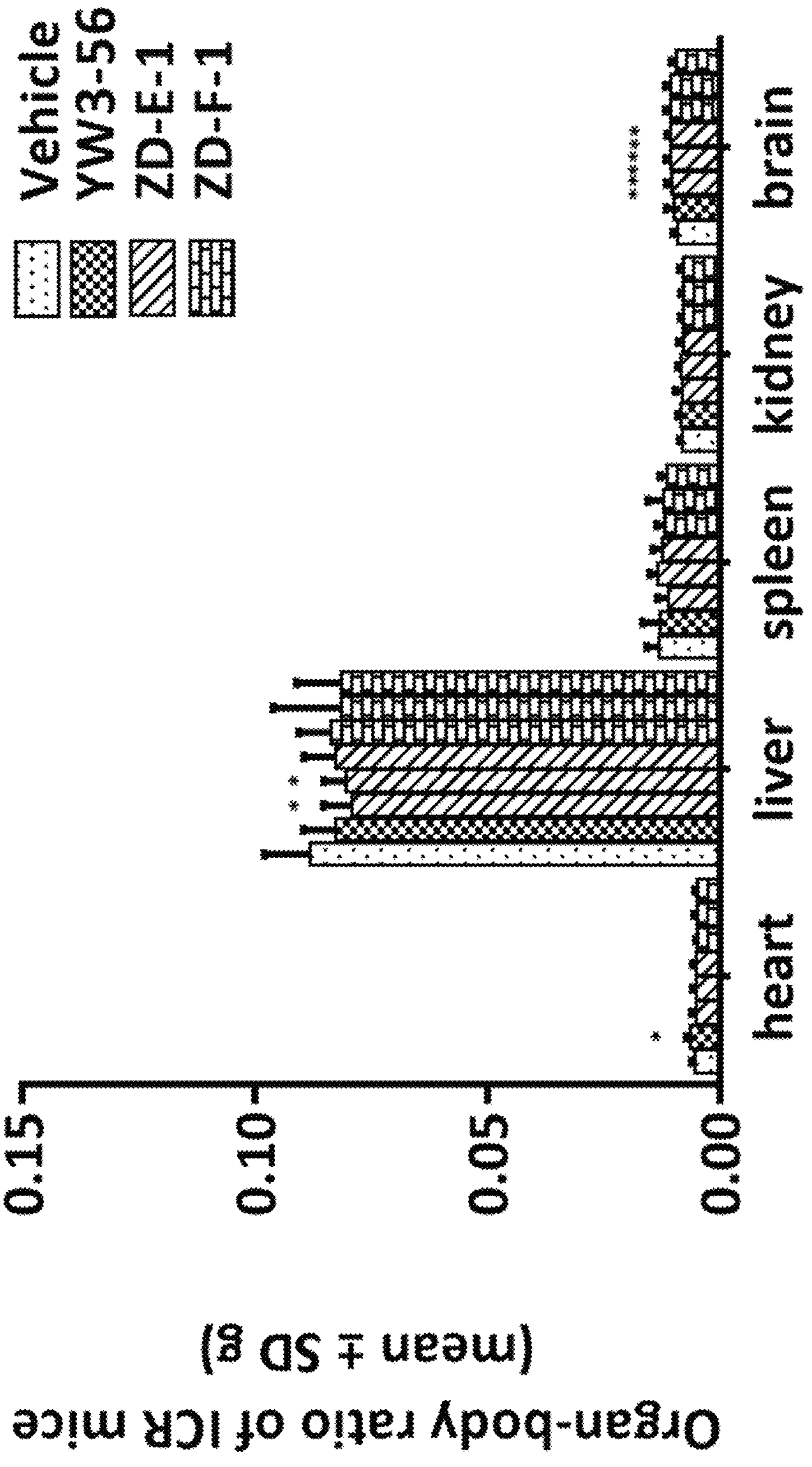
FIG. 5 shows statistics of a viscera-weight ratio of mice injected with the compounds ZD-E-1 and ZD-F-1.

As shown in FIG. 4, the tumor growth trends of compounds ZD-E-1 and ZD-F-1 in mice were roughly the same; however, after the 3rd day, the tumor size gradually changed, which could support the results of tumor weight. As shown in FIG. 5, by comparing the mouse viscera-weight ratios of the two compounds, it was found that: the effects on liver weight at high dosages (10 μmol/kg and 5 μmol/kg) and on brain weight at three dosages by the ZD-E-1 were different from those in the Vehicle group; however, the ZD-F-1 had no difference in liver weight and brain weight. The experimental results showed that ZD-E-1 was better than ZD-F-1 in inhibiting tumor growth, but had more obvious toxic side effects, causing liver failure and brain lesions in mice.

Test Example 4 Evaluation of Intracellular Distribution of Compounds ZD-B and ZD-E-1 (by Confocal Laser)

Tested cell line: U2Os (human osteosarcoma cells): purchased from Nanjing KeyGen Biotech. Inc.

A specific process was as follows:

1) Cell inoculation: a PBS buffer, a McCoy's 5A medium containing 10% fetal bovine serum, and a trypsin-EDTA digestion solution were preheated in a 37° C. water bath for 15 min. U2Os cells in well growth condition and in a logarithmic growth phase were selected, the original medium in the bottle was discarded, the cells were rinsed with 1 mL of the PBS buffer twice, added with 1 mL of the trypsin-EDTA digestion solution, and incubated in a cell culture incubator for 2 min (suspension cells did not need to be digested). When it was observed under a microscope that the cells became round and could fall off the wall of the flask, 1 mL of a medium was added to stop the digestion, and the cells were completely detached and dispersed by blowing gently with a dropper; the treated cells were transferred to a 15 mL centrifuge tube, centrifuged at 3,000 rpm for 3 min to discard a supernatant, re-added into 3 mL of the medium, and gently blown with a pipette to disperse evenly. After the cells were diluted 10 times in a 2 mL EP tube, 10 μL of a resulting cell suspension was drawn and counted under a microscope on a cell counting plate; total number of cells=(total number of cells in four grids/4)×10000× dilution factor. The cell suspension was diluted with the medium to a cell concentration of $1\times10^5$ cells/mL, and evenly inoculated into confocal small dishes, at 1 mL per dish. The inoculated confocal dishes were incubated in a cell culture incubator at 37° C. and 5% $CO_2$ for 8 h.

2) Administration: the growth and adhesion of cells were observed; when the cell adhesion rate reached more than 50%, 250 μL of each of the test sample solutions with a final concentration of 10 μM and 5 μM were administrated according to the preset group. The cells were gently tapped to disperse evenly, and incubated in the cell culture incubator for 8 h and 24 h separately.

3) Fixation: after taking out the confocal small dishes at different time points, the medium was removed by careful drawing; the cells were rinsed with a PBS buffer 3 times, added with 1 mL of a 4% paraformaldehyde fixative solution, and fixated at a room temperature for 30 min.

4) Staining: after aspirating the fixative solution, the cells were rinsed with PBS buffer 3 times; 1 mL of a freshly-prepared 0.5 μg/mL (1:10000) DAPI solution was added to the cells, stained for 3 min to 5 min, and then rinsed with the PBS buffer 3 times.

5) Observation: the cells were added with a PBS buffer (5 μL+995 μL PBS) containing an anti-fluorescent quencher, and observed under a fluorescence microscope or confocal laser.

Figure 6A:
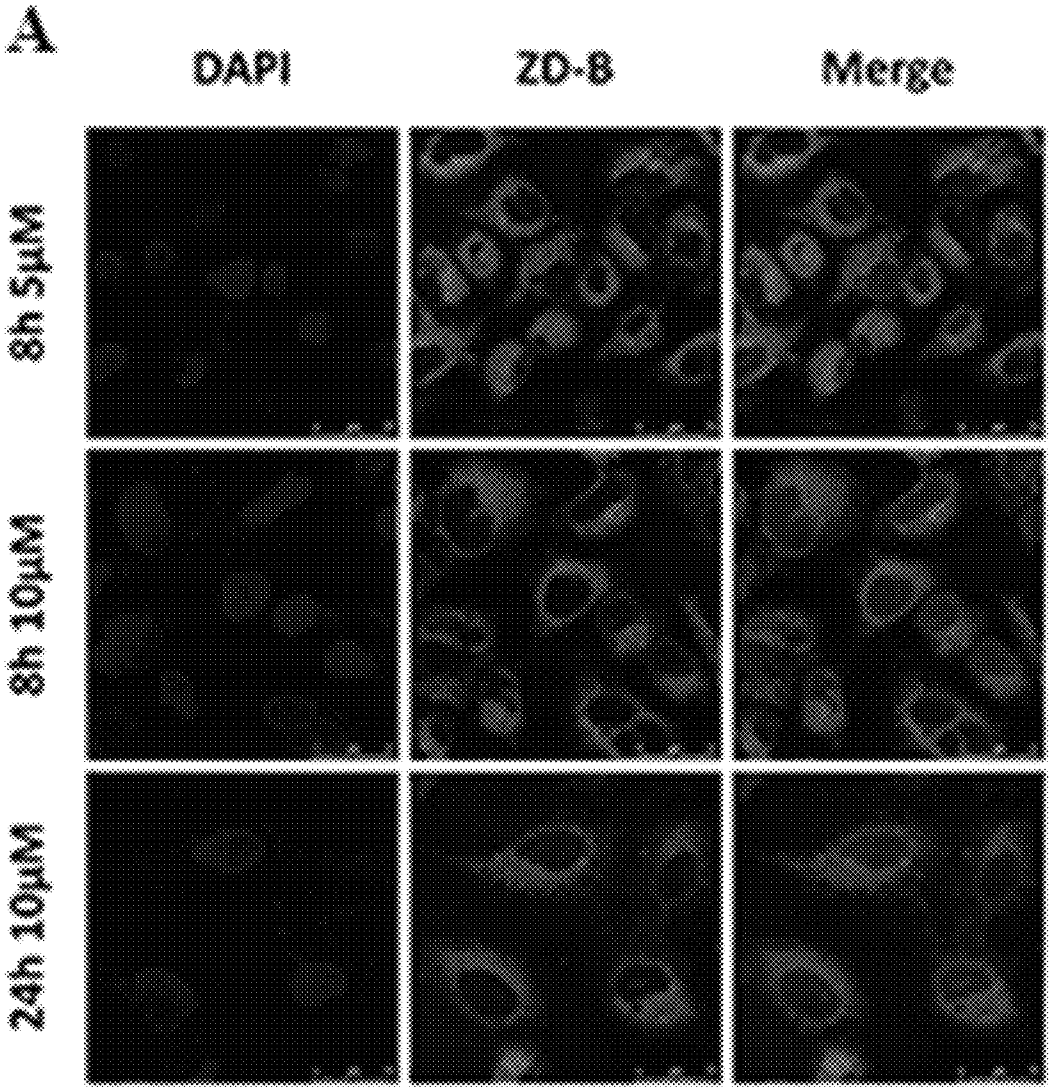
FIG. 6A-B show fluorescence co-localization of the compounds ZD-B and ZD-E-1 in U2Os cells.
Figure 6B:
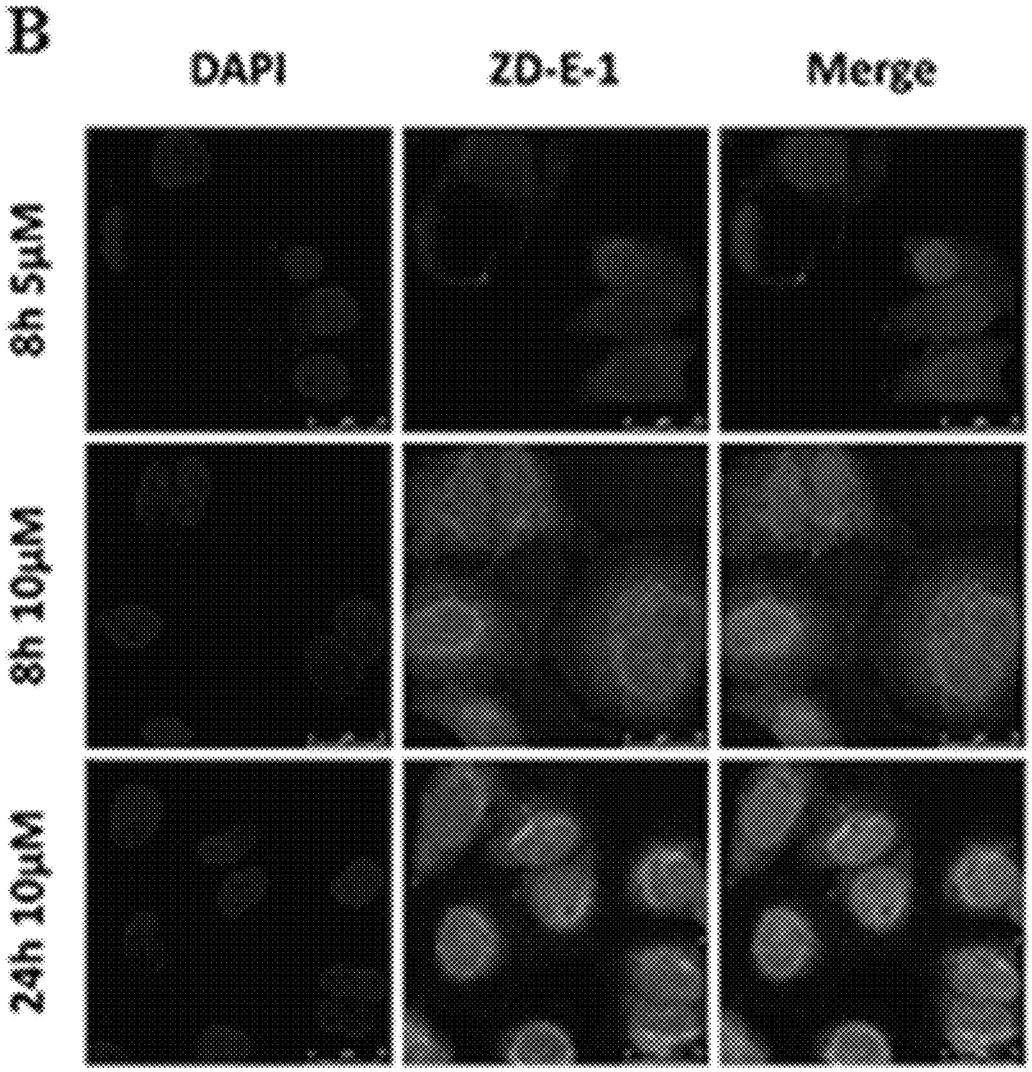

The results were shown in FIG. 6A-B (the cell nucleus was stained by DAPI, showing blue; the fluorescence of the compound showed green (Ex=480 nm; Em=520 nm); Merge was an overlay of the two); in FIGS. 6A-B, A was the ZD-B, and B was the ZD-E-1. It was seen from FIG. 6A-B that the compound ZD-B did not enter the nucleus, but was dispersed in the cytoplasm, indicating that a target point of the ZD-B was not PAD4 in the nucleus, and an inhibitory effect of the ZD-B on cancer cell proliferation might involve other mechanisms of action. However, ZD-E-1 was distributed in both the nucleus and cytoplasm; and had an increasing content entering the cell with an increase of concentration and the extension of time. This proved that ZD-E-1 could inhibit the proliferation of cancer cells by acting on the PAD4 pathway.

The above descriptions are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A fluorescently-traceable amino acid derivative, having a structure shown in formula I:

formula I

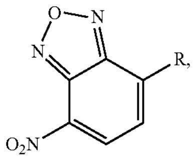

wherein, in formula I, R is any one of the groups shown in formula 1 to formula 10:

formula 1

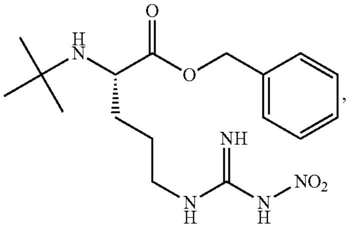

formula 2

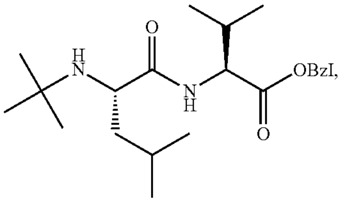

formula 3

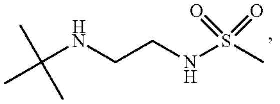

formula 4

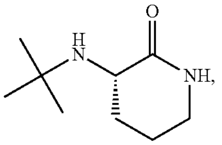

formula 5

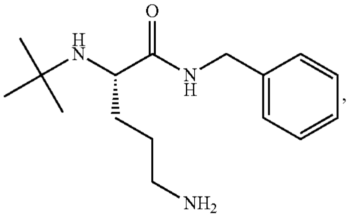

formula 6

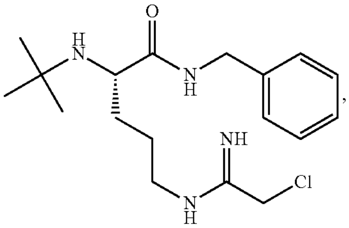

formula 7

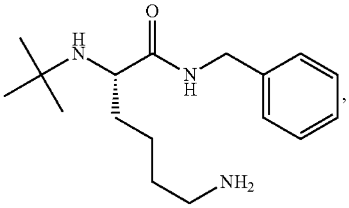

-continued
formula 8
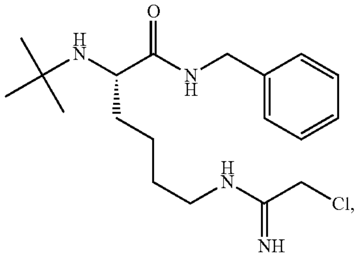
formula 9
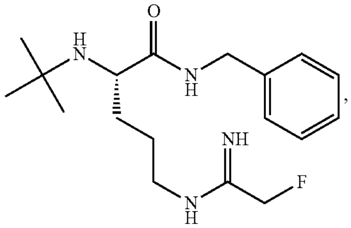
and
formula 10
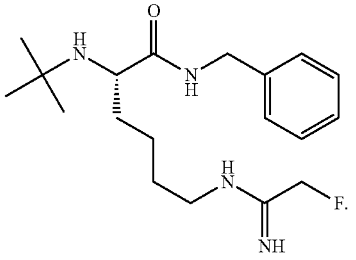
2. The fluorescently-traceable amino acid derivative according to claim 1, wherein the fluorescently-traceable amino acid derivative is any one selected from the group consisting of compounds shown in formula I-1 to formula I-10:
formula I-1
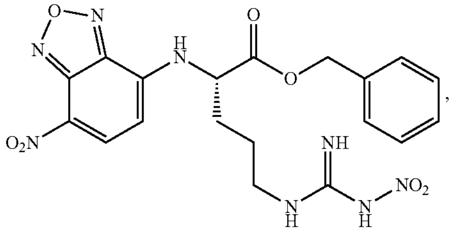
formula I-2
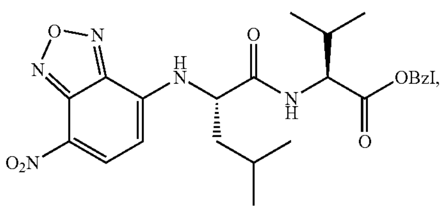
formula I-3
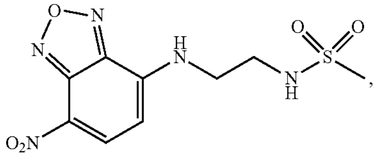
-continued
formula I-4
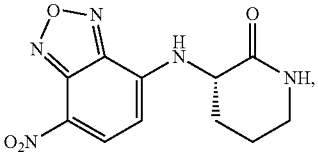
formula I-5
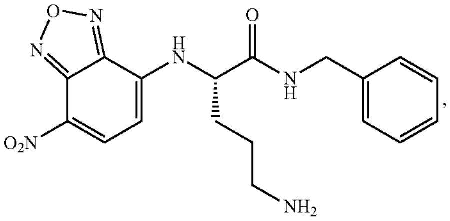
formula I-6
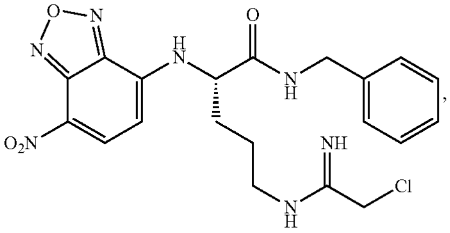
formula I-7
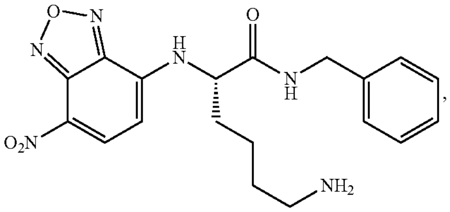
formula I-8
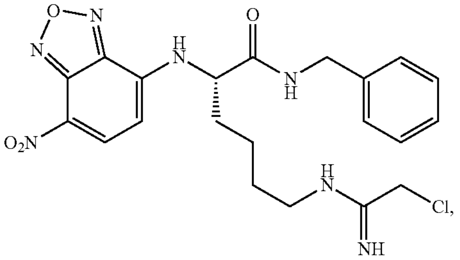
formula I-9
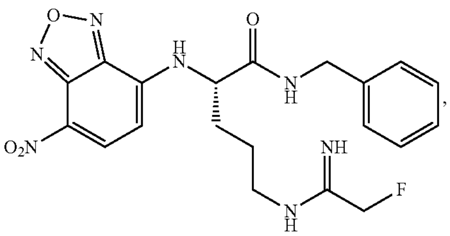

-continued formula I-10

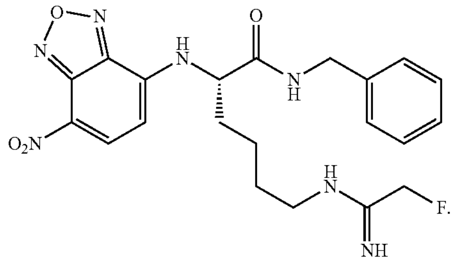

3. The fluorescently-traceable amino acid derivative according to claim 1, wherein when the fluorescently-traceable amino acid derivative is the compound shown in formula I-5, formula I-7, or formula I-8, the fluorescently-traceable amino acid derivative is a hydrochloride of the amino acid derivative.

4. A preparation method of the fluorescently-traceable amino acid derivative according to claim 1, wherein (i) when R is the group shown in formula 1, formula 2, or formula 3, the preparation method of the fluorescently-traceable amino acid derivative comprises the following steps:

mixing 4-chloro-7-nitro-2,1,3-benzoxadiazole, methanol, and a first reaction raw material, adjusting a resulting mixed solution to a pH value of 9.5 to 10.5 with N,N-diisopropylethylamine, and conducting substitution in the dark to obtain the fluorescently-traceable amino acid derivative; wherein the first reaction raw material is selected from the group consisting of Tos·Arg($NO_2$)-OBzl, HCl·LV-OBzl, and N-(2-aminoethyl) methanesulfonamide;

(ii) when R is the group shown in formula 4, the preparation method of the fluorescently-traceable amino acid derivative comprises the following steps:

mixing 4-chloro-7-nitro-2,1,3-benzoxadiazole, methanol, and a second reaction raw material, adjusting a resulting mixed solution to a pH value of 9.5 to 10.5 with N,N-diisopropylethylamine, and conducting substitution in the dark to obtain a first intermediate product;

dissolving the first intermediate product in ethyl acetate, mixing a resulting mixed solution with an ethyl acetate solution of HCl, and conducting hydrolysis to obtain a second intermediate product; and dissolving the second intermediate product in methanol, adjusting a resulting mixed solution to a pH value of 9.5 to 10.5 with triethylamine, and conducting ammonia substitution in the dark to obtain the fluorescently-traceable amino acid derivative; wherein the second reaction raw material has a structural formula as follows:

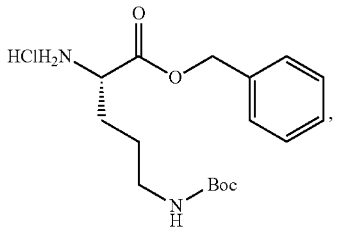

the first intermediate product has a structural formula as follows:

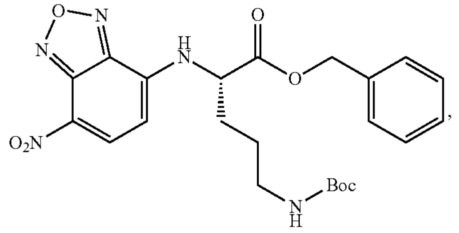 [SMILES: CC(C)(C)OC(=O)NCCC[C@H](Nc1ccc([N+](=O)[O-])c2nonc12)C(=O)OCc1ccccc1]

the second intermediate product has a structural formula as follows:

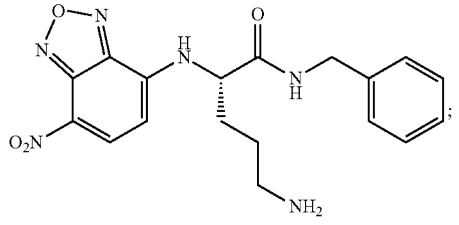 [SMILES: NCCC[C@H](Nc1ccc([N+](=O)[O-])c2nonc12)C(=O)NCc1ccccc1]

(iii) when R is the group shown in formula 5 or formula 7, the preparation method of the fluorescently-traceable amino acid derivative comprises the following steps:

dissolving a third reaction raw material in tetrahydrofuran, mixing a resulting mixed solution I with 1-hydroxybenzotriazole and dicyclohexylcarbodiimide to conduct activation, mixing a resulting activation system with benzylamine, adjusting an obtained mixed solution II to a pH value of 8 to 9 with N-methylmorpholine, and conducting condensation to obtain a third intermediate product;

dissolving the third intermediate product in methanol, and conducting hydrogenolysis in a hydrogen atmosphere in the presence of palladium on carbon to obtain a fourth intermediate product;

dissolving the fourth intermediate product and 4-chloro-7-nitro-2,1,3-benzoxadiazole in methanol, adjusting a resulting mixed solution to a pH value of 9.5 to 10.5 with N,N-diisopropylethylamine, and conducting substitution to obtain a fifth intermediate product; and dissolving the fifth intermediate product in ethyl acetate, mixing a resulting mixed solution with an ethyl acetate solution of HCl, and conducting hydrolysis to obtain the fluorescently-traceable amino acid derivative; wherein the third reaction raw material has a structural formula as follows:

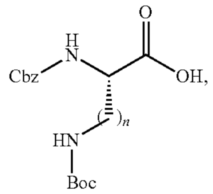

the third intermediate product has a structural formula as follows:

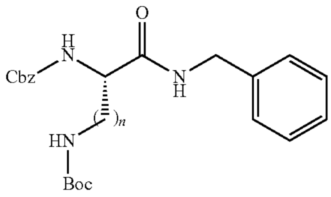, the fourth intermediate product has a structural formula as follows:

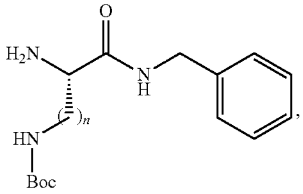, the fifth intermediate product has a structural formula as follows:

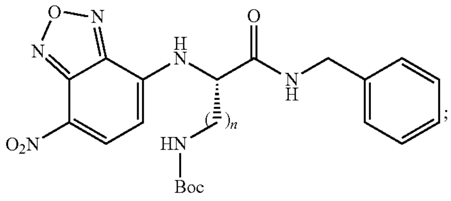;

and (iv) when R is the group shown in formula 6, formula 8, formula 9, or formula 10, the preparation method of the fluorescently-traceable amino acid derivative comprises the following steps:

mixing the fourth reaction raw material, the fifth reaction raw material, and methanol, adjusting a resulting mixed solution to a pH value of 9.5 to 10.5 with N,N-diisopropylethylamine, and conducting substitution to obtain the fluorescently-traceable amino acid derivative; wherein the fifth reaction raw material is selected from the group consisting of ethyl 2-chloroacetimidate and ethyl 2-fluoroacetimidate, and the fourth reaction raw material has a structural formula as follows:

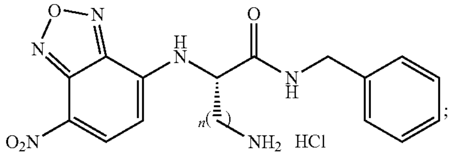;

and in the structural formulas of the third reaction raw material, the third intermediate product, the fourth intermediate product, the fifth intermediate product, and the fourth reaction raw material, n is 3 or 4.

5. The preparation method according to claim 4, wherein the fluorescently-traceable amino acid derivative is any one selected from the group consisting of compounds shown in formula I-1 to formula I-10:

formula I-1

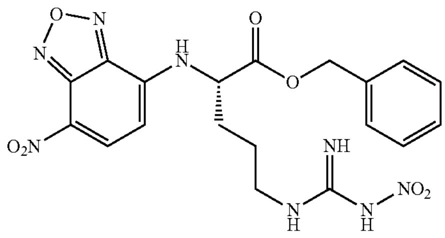, formula I-2

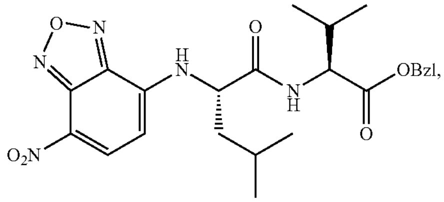, formula I-3

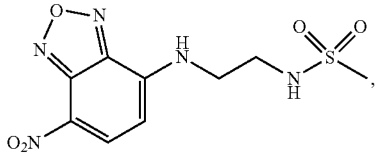, formula I-4

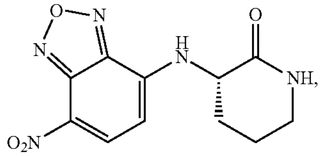, formula I-5

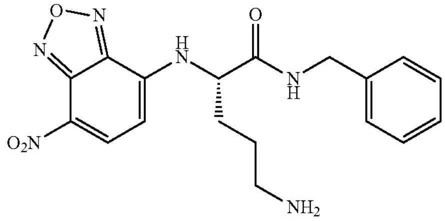, formula I-6

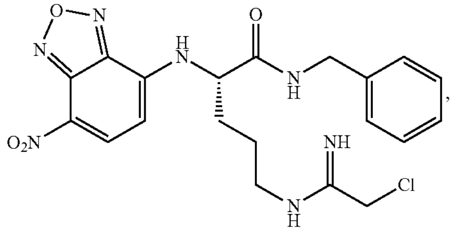,

-continued formula I-7

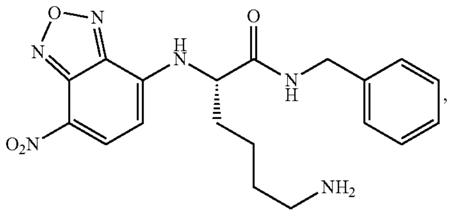

formula I-8

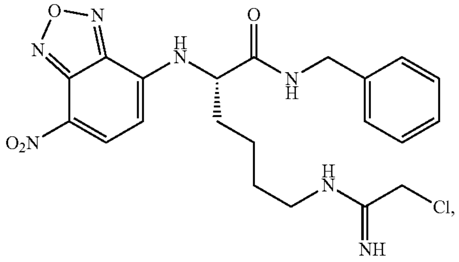

formula I-9

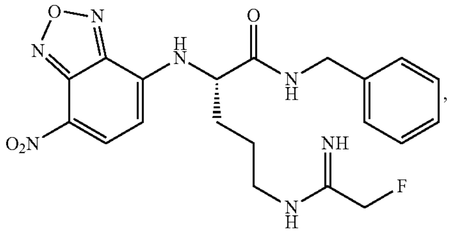

formula I-10

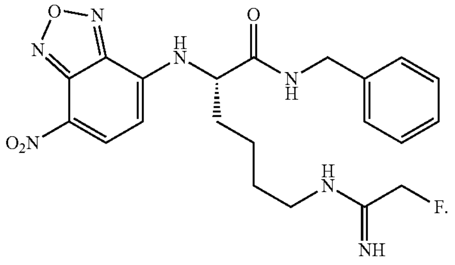

6. The preparation method according to claim 4, wherein when the fluorescently-traceable amino acid derivative is the compound shown in formula I-5, formula I-7, or formula I-8, the fluorescently-traceable amino acid derivative is a hydrochloride of the amino acid derivative.

7. The preparation method according to claim 4, wherein in (i), the substitution is conducted at 15° C. to 35° C.

8. The preparation method according to claim 4, wherein in (ii), the substitution is conducted at 15° C. to 35° C., the hydrolysis is conducted in an ice bath, and the ammonia substitution is conducted in an ice bath.

9. The preparation method according to claim 4, wherein in (iii), the condensation, the hydrogenolysis, and the substitution each are conducted at 15° C. to 35° C., and the hydrolysis is conducted in an ice bath.

10. The preparation method according to claim 4, wherein in (iv), the substitution is conducted at 15° C. to 35° C.

11. A method for treating a tumor, comprising administrating the fluorescently-traceable amino acid derivative according to claim 1 to a subject in need thereof.

12. The method according to claim 11, wherein the fluorescently-traceable amino acid derivative is any one selected from the group consisting of compounds shown in formula I-1 to formula I-10:

formula I-1

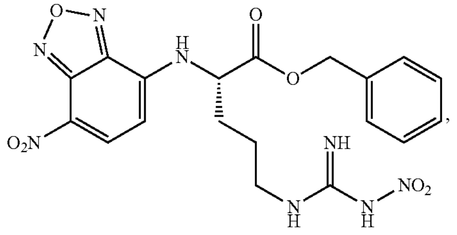

formula I-2

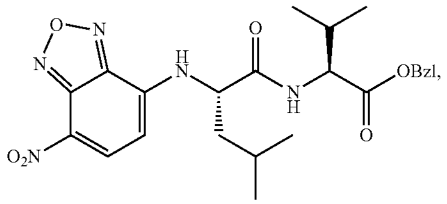

formula I-3

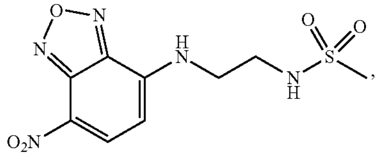

formula I-4

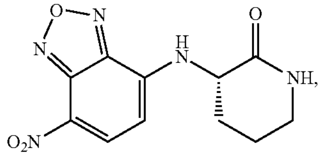

formula I-5

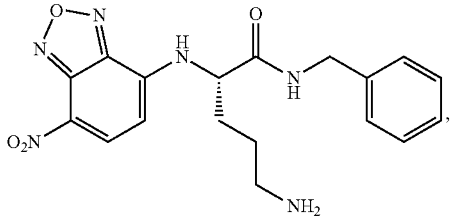

formula I-6

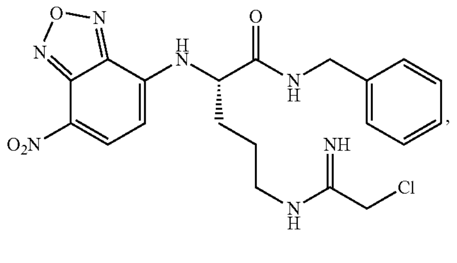

-continued formula I-7

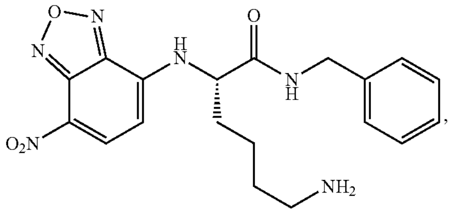

, formula I-8

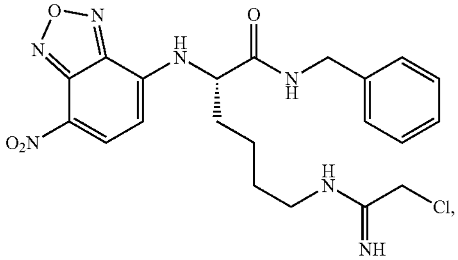

, formula I-9

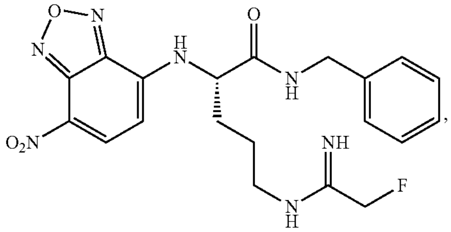

, and formula I-10

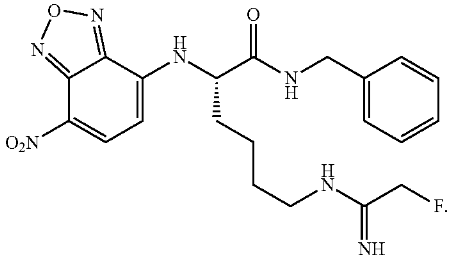

.

13. The method according to claim 11, wherein when the fluorescently-traceable amino acid derivative is the compound shown in formula I-5, formula I-7, or formula I-8, the fluorescently-traceable amino acid derivative is a hydrochloride of the amino acid derivative.

14. The method according to claim 11, wherein the tumor comprises lung cancer, colon cancer, osteosarcoma, or breast cancer.

15. The fluorescently-traceable amino acid derivative according to claim 1, wherein when the fluorescently-traceable amino acid derivative is the compound shown in formula I-1, a dosage is 2 μmol/kg, 5 μmol/kg, or 10 μmol/kg;

when the fluorescently-traceable amino acid derivative is the compound shown in formula I-2, the dosage is 2 μmol/kg, 5 μmol/kg, or 10 μmol/kg;

when the fluorescently-traceable amino acid derivative is the compound shown in formula I-3, the dosage is 10 μmol/kg;

when the fluorescently-traceable amino acid derivative is the compound shown in formula I-4, the dosage is 10 μmol/kg;

when the fluorescently-traceable amino acid derivative is the compound shown in formula I-5, the dosage is 10 μmol/kg;

when the fluorescently-traceable amino acid derivative is the compound shown in formula I-6, the dosage is 2 μmol/kg, 5 μmol/kg, or 10 μmol/kg; and when the fluorescently-traceable amino acid derivative is the compound shown in formula I-8, the dosage is 2 μmol/kg, 5 μmol/kg, or 10 μmol/kg.

16. The fluorescently-traceable amino acid derivative according to claim 2, wherein when the fluorescently-traceable amino acid derivative is the compound shown in formula I-1, a dosage is 2 μmol/kg, 5 μmol/kg, or 10 μmol/kg;

when the fluorescently-traceable amino acid derivative is the compound shown in formula I-2, the dosage is 2 μmol/kg, 5 μmol/kg, or 10 μmol/kg;

when the fluorescently-traceable amino acid derivative is the compound shown in formula I-3, the dosage is 10 μmol/kg;

when the fluorescently-traceable amino acid derivative is the compound shown in formula I-4, the dosage is 10 μmol/kg;

when the fluorescently-traceable amino acid derivative is the compound shown in formula I-5, the dosage is 10 μmol/kg;

when the fluorescently-traceable amino acid derivative is the compound shown in formula I-6, the dosage is 2 μmol/kg, 5 μmol/kg, or 10 μmol/kg; and when the fluorescently-traceable amino acid derivative is the compound shown in formula I-8, the dosage is 2 μmol/kg, 5 μmol/kg, or 10 μmol/kg.

17. The fluorescently-traceable amino acid derivative according to claim 3, wherein when the fluorescently-traceable amino acid derivative is the compound shown in formula I-1, a dosage is 2 μmol/kg, 5 μmol/kg, or 10 μmol/kg;

when the fluorescently-traceable amino acid derivative is the compound shown in formula I-2, the dosage is 2 μmol/kg, 5 μmol/kg, or 10 μmol/kg;

when the fluorescently-traceable amino acid derivative is the compound shown in formula I-3, the dosage is 10 μmol/kg;

when the fluorescently-traceable amino acid derivative is the compound shown in formula I-4, the dosage is 10 μmol/kg;

when the fluorescently-traceable amino acid derivative is the compound shown in formula I-5, the dosage is 10 μmol/kg;

when the fluorescently-traceable amino acid derivative is the compound shown in formula I-6, the dosage is 2 μmol/kg, 5 μmol/kg, or 10 μmol/kg; and when the fluorescently-traceable amino acid derivative is the compound shown in formula I-8, the dosage is 2 μmol/kg, 5 μmol/kg, or 10 μmol/kg.

18. The fluorescently-traceable amino acid derivative according to claim 1, wherein when the fluorescently-traceable amino acid derivative is the compound shown in formula I-1 or formula I-2, intraperitoneal injection is adopted; and when the fluorescently-traceable amino acid derivative is the compound shown in formula I-6 or formula I-8, the intraperitoneal injection or intravenous injection is adopted.

19. The fluorescently-traceable amino acid derivative according to claim 2, wherein when the fluorescently-traceable amino acid derivative is the compound shown in formula I-1 or formula I-2, intraperitoneal injection is adopted; and when the fluorescently-traceable amino acid derivative is the compound shown in formula I-6 or formula I-8, the intraperitoneal injection or intravenous injection is adopted.

20. The fluorescently-traceable amino acid derivative according to claim 3, wherein when the fluorescently-traceable amino acid derivative is the compound shown in formula I-1 or formula I-2, intraperitoneal injection is adopted; and when the fluorescently-traceable amino acid derivative is the compound shown in formula I-6 or formula I-8, the intraperitoneal injection or intravenous injection is adopted.

* * * * *